United States Patent
Braido et al.

(10) Patent No.: US 10,874,510 B2
(45) Date of Patent: Dec. 29, 2020

(54) PARAVALVULAR SEALING VIA EXTENDED CUFF MECHANISMS

(71) Applicant: St. Jude Medical, Cardiology Division, Inc., St. Paul, MN (US)

(72) Inventors: Peter N. Braido, Wyoming, MN (US); Yousef F. Alkhatib, Edina, MN (US); Steven Frederick Anderl, Forest Lake, MN (US); Jacob John Daly, Blaine, MN (US); Mina S. Fahim, Shoreview, MN (US); Kent J. Smith, Shoreview, MN (US); Ralph Joseph Thomas, Champlin, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 255 days.

(21) Appl. No.: 16/175,164

(22) Filed: Oct. 30, 2018

(65) Prior Publication Data
US 2019/0060065 A1    Feb. 28, 2019

Related U.S. Application Data

(63) Continuation of application No. 15/128,909, filed as application No. PCT/US2015/011387 on Jan. 14, 2015, now Pat. No. 10,143,551.
(Continued)

(51) Int. Cl.
*A61F 2/24* (2006.01)

(52) U.S. Cl.
CPC .......... *A61F 2/2418* (2013.01); *A61F 2/2436* (2013.01); *A61F 2/2439* (2013.01); *A61F 2250/0069* (2013.01)

(58) Field of Classification Search
CPC .... A61F 2/2436; A61F 2/2439; A61F 2/2442; A61F 2/246; A61F 2/2463; A61F 2250/0069; A61F 2/2418
See application file for complete search history.

(56) References Cited

U.S. PATENT DOCUMENTS

| 3,657,744 A | 4/1972 | Ersek |
| 4,275,469 A | 6/1981 | Gabbay |

(Continued)

FOREIGN PATENT DOCUMENTS

| DE | 19857887 A1 | 7/2000 |
| DE | 10121210 B4 | 11/2005 |

(Continued)

OTHER PUBLICATIONS

Braido, Peter N., U.S. Appl. No. 61/931,265, filed Jan. 24, 2014; Stationary Intra-Annular Halo Designs for Paravalvular Leak (PVL) Reduction—Active Channel Filling Cuff Designs.
(Continued)

*Primary Examiner* — Katrina M Stransky
(74) *Attorney, Agent, or Firm* — Lerner, David, Littenberg, Krumholz & Mentlik, LLP

(57) ABSTRACT

A prosthetic heart valve may include a collapsible and expandable stent having a proximal end, a distal end, an annulus section adjacent the proximal end, and a plurality of cells connected to one another in annular rows around the stent, a cuff attached to the stent, and a sealing member attached to the cuff and extending from a proximal end of the cuff to a free edge. The sealing member may be movable between an extended condition in which the free edge is located proximally of the proximal end of the stent, and an inverted condition in which the free edge is located distally of the proximal end of the stent and a first surface of the sealing member confronts an outward-facing surface of the cuff. Various mechanisms for moving the sealing member are also described.

14 Claims, 12 Drawing Sheets

Related U.S. Application Data

(60) Provisional application No. 61/972,831, filed on Mar. 31, 2014.

(56) References Cited

U.S. PATENT DOCUMENTS

| | | |
|---|---|---|
| 4,423,730 A | 1/1984 | Gabbay |
| 4,491,986 A | 1/1985 | Gabbay |
| 4,759,758 A | 7/1988 | Gabbay |
| 4,816,029 A | 3/1989 | Penny, III et al. |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,415,664 A | 5/1995 | Pinchuk |
| 5,480,423 A | 1/1996 | Ravenscroft et al. |
| 5,843,167 A | 12/1998 | Dwyer et al. |
| 5,855,601 A | 1/1999 | Bessler et al. |
| 5,924,424 A | 7/1999 | Stevens et al. |
| 5,935,163 A | 8/1999 | Gabbay |
| 5,961,549 A | 10/1999 | Nguyen et al. |
| 5,968,068 A | 10/1999 | Dehdashtian et al. |
| 6,045,576 A | 4/2000 | Starr et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,306,141 B1 | 10/2001 | Jervis |
| 6,368,348 B1 | 4/2002 | Gabbay |
| 6,419,695 B1 | 7/2002 | Gabbay |
| 6,458,153 B1 | 10/2002 | Bailey et al. |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,652,578 B2 | 11/2003 | Bailey et al. |
| 6,685,625 B2 | 2/2004 | Gabbay |
| 6,716,244 B2 | 4/2004 | Klaco |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 6,951,573 B1 | 10/2005 | Dilling |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,195,641 B2 | 3/2007 | Palmaz et al. |
| 7,247,167 B2 | 7/2007 | Gabbay |
| 7,267,686 B2 | 9/2007 | DiMatteo et al. |
| 7,276,078 B2 | 10/2007 | Spenser et al. |
| 7,311,730 B2 | 12/2007 | Gabbay |
| 7,320,704 B2 | 1/2008 | Lashinski et al. |
| 7,329,278 B2 | 2/2008 | Seguin et al. |
| 7,374,573 B2 | 5/2008 | Gabbay |
| 7,381,218 B2 | 6/2008 | Schreck |
| 7,381,219 B2 | 6/2008 | Salahieh et al. |
| 7,452,371 B2 | 11/2008 | Pavcnik et al. |
| 7,510,572 B2 | 3/2009 | Gabbay |
| 7,510,575 B2 | 3/2009 | Spenser et al. |
| 7,524,331 B2 | 4/2009 | Birdsall |
| 7,534,261 B2 | 5/2009 | Friedman |
| RE40,816 E | 6/2009 | Taylor et al. |
| 7,585,321 B2 | 9/2009 | Cribier |
| 7,628,805 B2 | 12/2009 | Spenser et al. |
| 7,682,390 B2 | 3/2010 | Seguin |
| 7,708,775 B2 | 5/2010 | Rowe et al. |
| 7,731,742 B2 | 6/2010 | Schlick et al. |
| 7,748,389 B2 | 7/2010 | Salahieh et al. |
| 7,780,725 B2 | 8/2010 | Haug et al. |
| 7,799,069 B2 | 9/2010 | Bailey et al. |
| 7,803,185 B2 | 9/2010 | Gabbay |
| 7,824,442 B2 | 11/2010 | Salahieh et al. |
| 7,837,727 B2 | 11/2010 | Goetz et al. |
| 7,846,203 B2 | 12/2010 | Cribier |
| 7,846,204 B2 | 12/2010 | Letac et al. |
| 7,857,845 B2 | 12/2010 | Stacchino et al. |
| 7,892,281 B2 | 2/2011 | Seguin et al. |
| 7,914,569 B2 | 3/2011 | Nguyen et al. |
| 7,959,666 B2 | 6/2011 | Salahieh et al. |
| 7,959,672 B2 | 6/2011 | Salahieh et al. |
| 7,972,378 B2 | 7/2011 | Tabor et al. |
| 7,988,724 B2 | 8/2011 | Salahieh et al. |
| 7,993,394 B2 | 8/2011 | Hariton et al. |
| 8,016,877 B2 | 9/2011 | Seguin et al. |
| D648,854 S | 11/2011 | Braido |
| 8,048,153 B2 | 11/2011 | Salahieh et al. |
| 8,052,741 B2 | 11/2011 | Bruszewski et al. |
| 8,052,749 B2 | 11/2011 | Salahieh et al. |
| 8,052,750 B2 | 11/2011 | Tuval et al. |
| 8,062,355 B2 | 11/2011 | Figulla et al. |
| 8,075,611 B2 | 12/2011 | Millwee et al. |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,137,398 B2 | 3/2012 | Tuval et al. |
| 8,142,497 B2 | 3/2012 | Friedman |
| D660,432 S | 5/2012 | Braido |
| D660,433 S | 5/2012 | Braido et al. |
| D660,967 S | 5/2012 | Braido et al. |
| 8,182,528 B2 | 5/2012 | Salahieh et al. |
| 8,221,493 B2 | 7/2012 | Boyle et al. |
| 8,230,717 B2 | 7/2012 | Matonick |
| 8,231,670 B2 | 7/2012 | Salahieh et al. |
| 8,252,051 B2 | 8/2012 | Chau et al. |
| 8,308,798 B2 | 11/2012 | Pintor et al. |
| 8,313,525 B2 | 11/2012 | Tuval et al. |
| 8,323,335 B2 | 12/2012 | Rowe et al. |
| 8,323,336 B2 | 12/2012 | Hill et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,998 B2 | 1/2013 | Pintor et al. |
| 8,366,769 B2 | 2/2013 | Huynh et al. |
| 8,403,983 B2 | 3/2013 | Quadri et al. |
| 8,408,214 B2 | 4/2013 | Spenser |
| 8,414,643 B2 | 4/2013 | Tuval et al. |
| 8,425,593 B2 | 4/2013 | Braido et al. |
| 8,449,599 B2 | 5/2013 | Chau et al. |
| 8,449,604 B2 | 5/2013 | Moaddeb et al. |
| D684,692 S | 6/2013 | Braido |
| 8,454,686 B2 | 6/2013 | Alkhatib |
| 8,500,798 B2 | 8/2013 | Rowe et al. |
| 8,568,474 B2 | 10/2013 | Yeung et al. |
| 8,579,962 B2 | 11/2013 | Salahieh et al. |
| 8,579,966 B2 | 11/2013 | Seguin et al. |
| 8,585,755 B2 | 11/2013 | Chau et al. |
| 8,591,575 B2 | 11/2013 | Cribier |
| 8,597,349 B2 | 12/2013 | Alkhatib |
| 8,603,159 B2 | 12/2013 | Seguin et al. |
| 8,603,160 B2 | 12/2013 | Salahieh et al. |
| 8,613,765 B2 | 12/2013 | Bonhoeffer et al. |
| 8,623,074 B2 | 1/2014 | Ryan |
| 8,652,204 B2 | 2/2014 | Quill et al. |
| 8,663,322 B2 | 3/2014 | Keranen |
| 8,668,733 B2 | 3/2014 | Haug et al. |
| 8,685,080 B2 | 4/2014 | White |
| 8,728,154 B2 | 5/2014 | Alkhatib |
| 8,747,459 B2 | 6/2014 | Nguyen et al. |
| 8,764,820 B2 | 7/2014 | Dehdashtian et al. |
| 8,795,357 B2 | 8/2014 | Yohanan et al. |

(56) References Cited

U.S. PATENT DOCUMENTS

| | | |
|---|---|---|
| 8,801,776 B2 | 8/2014 | House et al. |
| 8,808,356 B2 | 8/2014 | Braido et al. |
| 8,828,078 B2 | 9/2014 | Salahieh et al. |
| 8,834,563 B2 | 9/2014 | Righini |
| 8,840,661 B2 | 9/2014 | Manasse |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,940,040 B2 | 1/2015 | Shahriari |
| 8,945,209 B2 | 2/2015 | Bonyuet et al. |
| 8,961,595 B2 | 2/2015 | Alkhatib |
| 8,974,523 B2 | 3/2015 | Thill et al. |
| 8,974,524 B2 | 3/2015 | Yeung et al. |
| 9,326,856 B2 | 5/2016 | Schraut et al. |
| 9,889,004 B2 | 2/2018 | Braido |
| 2002/0036220 A1 | 3/2002 | Gabbay |
| 2003/0014104 A1 | 1/2003 | Cribier |
| 2003/0023303 A1 | 1/2003 | Palmaz et al. |
| 2003/0040792 A1 | 2/2003 | Gabbay |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0111111 A1 | 6/2004 | Lin |
| 2004/0186563 A1 | 9/2004 | Lobbi |
| 2004/0210304 A1 | 10/2004 | Seguin et al. |
| 2004/0260389 A1 | 12/2004 | Case et al. |
| 2005/0075720 A1 | 4/2005 | Nguyen et al. |
| 2005/0096726 A1 | 5/2005 | Sequin et al. |
| 2005/0137682 A1 | 6/2005 | Justino |
| 2005/0137687 A1 | 6/2005 | Salahieh et al. |
| 2005/0137695 A1 | 6/2005 | Salahieh et al. |
| 2005/0137697 A1 | 6/2005 | Salahieh et al. |
| 2005/0137701 A1 | 6/2005 | Salahieh et al. |
| 2005/0203605 A1 | 9/2005 | Dolan |
| 2005/0240200 A1 | 10/2005 | Bergheim |
| 2005/0256566 A1 | 11/2005 | Gabbay |
| 2006/0008497 A1 | 1/2006 | Gabbay |
| 2006/0074484 A1 | 4/2006 | Huber |
| 2006/0106415 A1 | 5/2006 | Gabbay |
| 2006/0122692 A1 | 6/2006 | Gilad et al. |
| 2006/0142848 A1 | 6/2006 | Gabbay |
| 2006/0149360 A1 | 7/2006 | Schwammenthal et al. |
| 2006/0161249 A1 | 7/2006 | Realyvasquez et al. |
| 2006/0167468 A1 | 7/2006 | Gabbay |
| 2006/0173532 A1 | 8/2006 | Flagle et al. |
| 2006/0178740 A1 | 8/2006 | Stacchino et al. |
| 2006/0195180 A1 | 8/2006 | Kheradvar et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0276874 A1 | 12/2006 | Wilson et al. |
| 2006/0287717 A1 | 12/2006 | Rowe et al. |
| 2007/0010876 A1 | 1/2007 | Salahieh et al. |
| 2007/0016285 A1 | 1/2007 | Lane et al. |
| 2007/0027534 A1 | 2/2007 | Bergheim et al. |
| 2007/0043431 A1 | 2/2007 | Melsheimer |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0073387 A1 | 3/2007 | Forster et al. |
| 2007/0073391 A1 | 3/2007 | Bourang et al. |
| 2007/0088431 A1 | 4/2007 | Bourang et al. |
| 2007/0093890 A1 | 4/2007 | Eliasen et al. |
| 2007/0100435 A1 | 5/2007 | Case et al. |
| 2007/0112422 A1 | 5/2007 | Dehdashtian |
| 2007/0118210 A1 | 5/2007 | Pinchuk |
| 2007/0162100 A1 | 7/2007 | Gabbay |
| 2007/0168013 A1 | 7/2007 | Douglas |
| 2007/0203575 A1 | 8/2007 | Forster et al. |
| 2007/0213813 A1 | 9/2007 | Von Segesser et al. |
| 2007/0233228 A1 | 10/2007 | Eberhardt et al. |
| 2007/0239271 A1 | 10/2007 | Nguyen |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147182 A1 | 6/2008 | Righini et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0054975 A1 | 2/2009 | del Nido et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0276027 A1 | 11/2009 | Glynn |
| 2009/0276040 A1 | 11/2009 | Rowe et al. |
| 2009/0287299 A1 | 11/2009 | Tabor et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0082094 A1 | 4/2010 | Quadri et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0168844 A1 | 7/2010 | Toomes et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0234940 A1 | 9/2010 | Dolan |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0054466 A1 | 3/2011 | Rothstein et al. |
| 2011/0098800 A1 | 4/2011 | Braido et al. |
| 2011/0098802 A1* | 4/2011 | Braido .................. A61F 2/243 623/1.26 |
| 2011/0137397 A1 | 6/2011 | Chau et al. |
| 2011/0172765 A1 | 7/2011 | Nguyen et al. |
| 2011/0208283 A1 | 8/2011 | Rust |
| 2011/0224678 A1 | 9/2011 | Gabbay |
| 2011/0238168 A1 | 9/2011 | Pellegrini et al. |
| 2011/0264206 A1 | 10/2011 | Tabor |
| 2011/0295363 A1 | 12/2011 | Girard et al. |
| 2012/0035722 A1 | 2/2012 | Tuval |
| 2012/0041550 A1 | 2/2012 | Salahieh et al. |
| 2012/0053681 A1 | 3/2012 | Alkhatib et al. |
| 2012/0071969 A1 | 3/2012 | Li et al. |
| 2012/0078347 A1 | 3/2012 | Braido et al. |
| 2012/0078350 A1 | 3/2012 | Wang et al. |
| 2012/0101572 A1 | 4/2012 | Kovalsky et al. |
| 2012/0123529 A1 | 5/2012 | Levi et al. |
| 2012/0143324 A1 | 6/2012 | Rankin et al. |
| 2012/0303116 A1 | 11/2012 | Gorman, III et al. |
| 2013/0018458 A1 | 1/2013 | Yohanan et al. |
| 2013/0274873 A1 | 10/2013 | Delaloye et al. |
| 2013/0304200 A1 | 11/2013 | McLean et al. |
| 2013/0331929 A1 | 12/2013 | Mitra et al. |
| 2014/0005771 A1 | 1/2014 | Braido et al. |
| 2014/0121763 A1 | 5/2014 | Duffy et al. |
| 2014/0155997 A1 | 6/2014 | Braido |
| 2014/0214159 A1 | 7/2014 | Vidlund et al. |
| 2014/0228946 A1 | 8/2014 | Chau et al. |

(56) References Cited

U.S. PATENT DOCUMENTS

| | | | |
|---|---|---|---|
| 2014/0303719 | A1 | 10/2014 | Cox et al. |
| 2014/0324164 | A1 | 10/2014 | Gross et al. |
| 2014/0343671 | A1 | 11/2014 | Yohanan et al. |
| 2014/0350668 | A1 | 11/2014 | Delaloye et al. |
| 2014/0350669 | A1 | 11/2014 | Gillespie et al. |

FOREIGN PATENT DOCUMENTS

| | | | |
|---|---|---|---|
| DE | 102005003632 A1 | 8/2006 | |
| DE | 202008009610 U1 | 12/2008 | |
| EP | 0850607 A1 | 7/1998 | |
| EP | 1000590 A1 | 5/2000 | |
| EP | 1584306 A1 | 10/2005 | |
| EP | 1598031 A2 | 11/2005 | |
| EP | 1360942 B1 | 12/2005 | |
| EP | 1926455 A2 | 6/2008 | |
| EP | 2537487 A1 | 12/2012 | |
| EP | 2870946 A1 | 5/2015 | |
| EP | 2898859 A1 | 7/2015 | |
| EP | 2898859 B1 | 11/2018 | |
| FR | 2850008 A1 | 7/2004 | |
| FR | 2847800 B1 | 10/2005 | |
| WO | 9117720 A1 | 11/1991 | |
| WO | 9716133 A1 | 5/1997 | |
| WO | 9832412 A2 | 7/1998 | |
| WO | 9913801 A1 | 3/1999 | |
| WO | 01028459 A1 | 4/2001 | |
| WO | 0149213 A2 | 7/2001 | |
| WO | 01054625 A1 | 8/2001 | |
| WO | 01056500 A2 | 8/2001 | |
| WO | 01076510 A2 | 10/2001 | |
| WO | 0236048 A1 | 5/2002 | |
| WO | 0247575 A2 | 6/2002 | |
| WO | 02067782 A2 | 9/2002 | |
| WO | 03047468 A1 | 6/2003 | |
| WO | 2005062980 A2 | 7/2005 | |
| WO | 2005070343 A1 | 8/2005 | |
| WO | 06073626 A2 | 7/2006 | |
| WO | 07071436 A2 | 6/2007 | |
| WO | 2008070797 A2 | 6/2008 | |
| WO | 2009024859 A2 | 2/2009 | |
| WO | 2009042196 A2 | 4/2009 | |
| WO | 2010008548 A2 | 1/2010 | |
| WO | 2010008549 A1 | 1/2010 | |
| WO | 2010096176 A1 | 8/2010 | |
| WO | 2010098857 A1 | 9/2010 | |
| WO | 2011133787 A1 | 10/2011 | |
| WO | 2012048035 A2 | 4/2012 | |
| WO | 2012177942 A2 | 12/2012 | |
| WO | 2013028387 A2 | 2/2013 | |
| WO | 2014163704 A1 | 10/2014 | |
| WO | 2014164149 | 10/2014 | |
| WO | 2014164151 A1 | 10/2014 | |
| WO | 2015077274 A1 | 5/2015 | |

OTHER PUBLICATIONS

Preliminary Opinion of the Opposition Division Indicating Issue of Summons to Follow at a Later Time and Shorter Notice for EP15152324.8 dated May 13, 2020; 12 pages.
Ruiz, Carlos, Overview of PRE-CE Mark Transcatheter Aortic Valve Technologies, Euro PCR—dated May 25, 2010.
Percutaneous aortic valve replacement: resection before implantation, 836-840, Quaden, Rene et al., European J. of cardio-thoracic Surgery, 27 (2005).
Braido et al., Design U.S. Appl. No. 29/375,243, filed Sep. 20, 2010.

Catheter-implanted prosthetic heart valves, Knudsen, L.L., et al., The International Journal of Artificial Organs, vol. 16, no. 5 1993, pp. 253-262.
Transluminal Aortic Valve Placement, Moazami, Nader, et al., ASAIO Journal, 1996; 42:M381-M385.
Transluminal Catheter Implanted Prosthetic Heart Valves, Andersen, Henning Rud, International Journal of Angiology 1:102-106 (1998).
Transluminal implantation of artificial heart valves, Andersen, H. R., et al., European Heart Journal (1992) 13, 704-708.
Is it Reasonable to Treat all Calcified Stenotic Aortic Valves With a Valved Stent?, 579-584, Zegdi, Rachid, MD, PhD et al., J. of the American College of Cardiology, vol. 51, No. 5, Feb. 5, 2008.
"Direct-Access Valve Replacement", Christoph H. Huber, et al., Journal of the American College of Cardiology, vol. 46, No. 2, (Jul. 19, 2005).
"Percutaneous Aortic Valve Implantation Retrograde From the Femoral Artery", John G. Webb et al., Circulation, 2006; 113:842-850 (Jun. 2, 2006).
"Minimally invasive cardiac surgery", M. J. Mack, Surgical Endoscopy, 2006, 20:S488-S492, DOI: 10.1007/s00464-006-0110-8 (presented Apr. 24, 2006).
"Transapical Transcatheter Aortic Valve Implantation in Humans", Samuel V. Lichtenstein et al., Circulation. 2006; 114: 591-596 (Jul. 31, 2006).
"Closed heart surgery: Back to the future", Samuel V. Lichtenstein, The Journal of Thoracic and Cardiovascular Surgery, vol. 131, No. 5, pp. 941-943.
"Transapical approach for sutureless stent-fixed aortic valve implantation: experimental results"; Th. Walther et al., European Journal of Cardio-thoracic Surgery 29 (2006) 703-708 (Jan. 30, 2006).
"Transapical aortic valve implantation: an animal feasibility study"; Todd M. Dewey et al., The annals of thoracic surgery 2006; 82: 110-6 (Feb. 13, 2006).
Textbook "Transcatheter Valve Repair", 2006, pp. 165-186.
Braido, Peter Nicholas, U.S. Appl. No. 29/375,260, filed Sep. 20, 2010, titled "Forked Ends".
Buellesfeld et al., Treatment of paravalvular leaks through inverventional techniques; Department of Cardiology, Ben University Hospital 2011.
De Cicco, Giuseppe, et al. "Aortic valve periprosthetic leakage: anatomic observations and surgical results." The Annals of thoracic surgery 79.5 (2005): 1480-1485.
Extended European Search Report for Application No. 15152315.6 dated May 29, 2015.
Extended European Search Report for Application No. 15152324.8 dated Jun. 10, 2015.
Gössl, Mario, and Charanjit S. Rihal. "Percutaneous treatment of aortic and mitral valve paravalvular regurgitation." Current cardiology reports 15.8 (2013): 1-8.
Heat Advisor, "Heart repairs without surgery. Minimally invasive procedures aim to correct valve leakage", Sep. 2004, PubMed ID 15586429.
International Search Report for Application No. PCT/US2014/054485 dated Nov. 20, 2014.
International Search Report for Application No. PCT/US2015/011387 dated Mar. 30, 2015.
Muñoz, et al., "Guidance of treatment of perivalvular prosthetic leaks.", Current cardiology reports, 16.430, 6 pages, Jan. 2014.
Rohde,et al., "Resection of Calcified Aortic Heart Leaflets In Vitro by Q-Switched 2 μm Microsecond Laser Radiation", Journal of Cardiac Surgery, 30(2):157-62. Feb. 2015.
Swiatkiewicz, Iwona, et al. "Percutaneous closure of mitral perivalvular leak." Kardiologia polska 67.7 (2009): 762.
Transcatheter Umbrella Closure of Valvular and Paravalvular Leaks, Hourihan et al., Journal of the American College of Cardiology, vol. 20, No. 6, pp. 1371-1377, (1992).

* cited by examiner

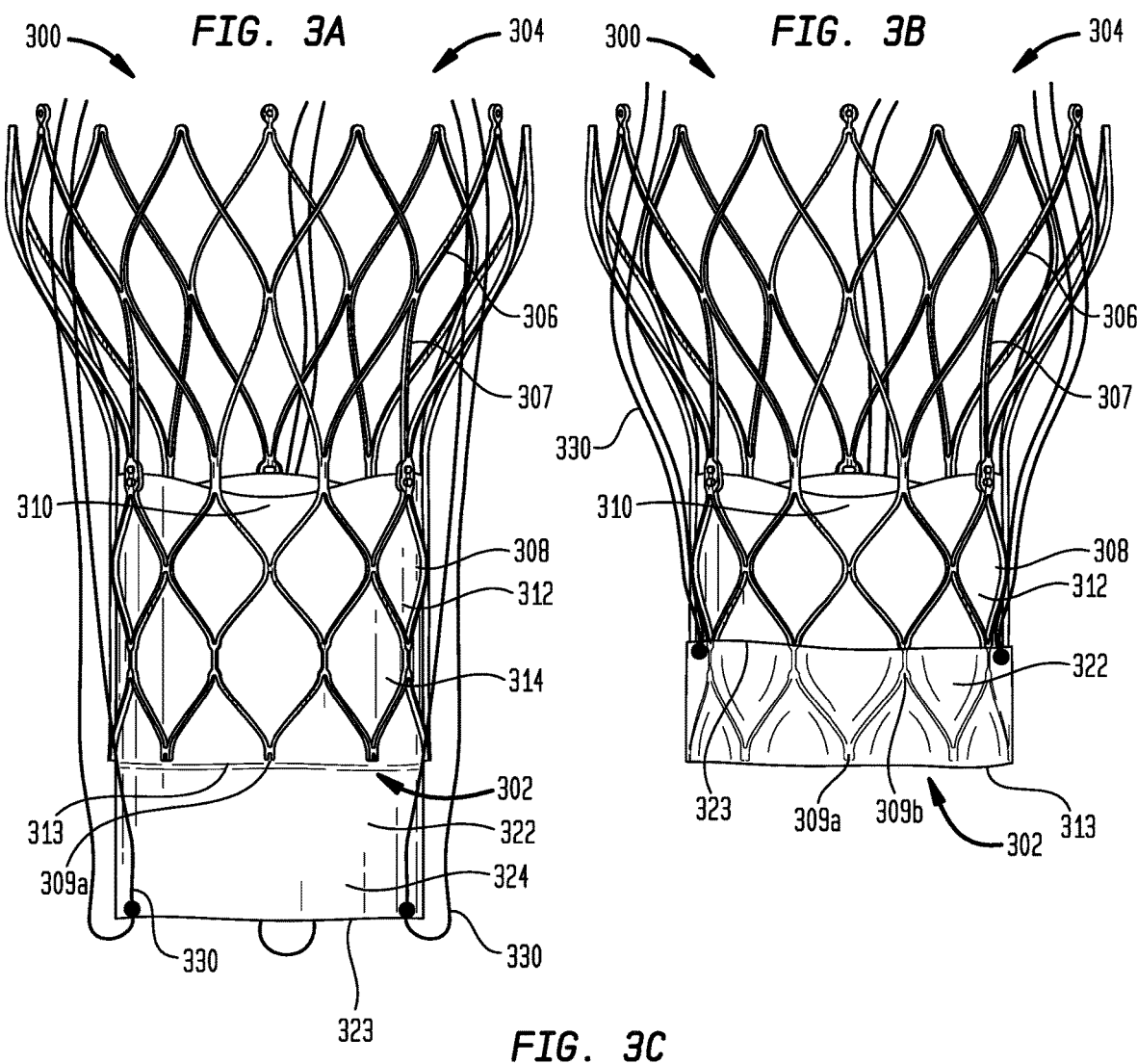
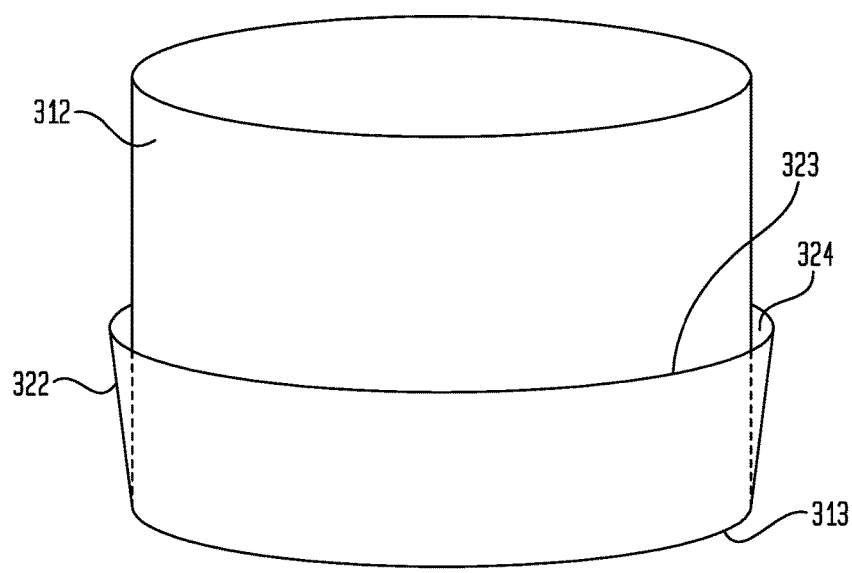

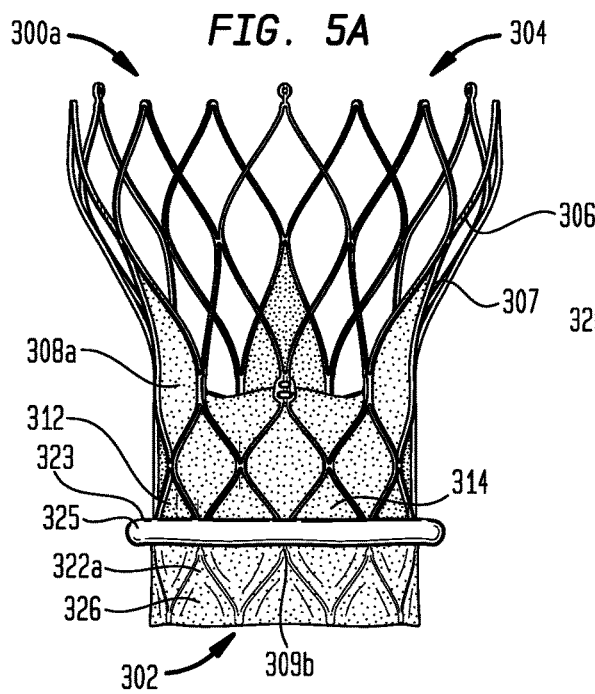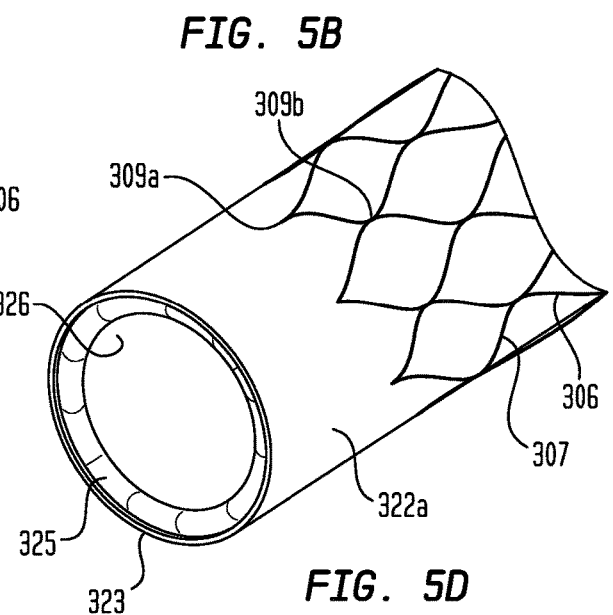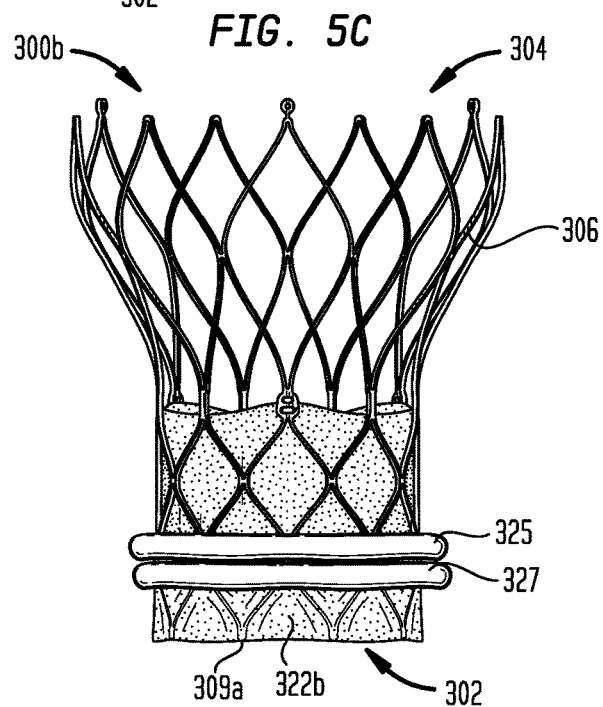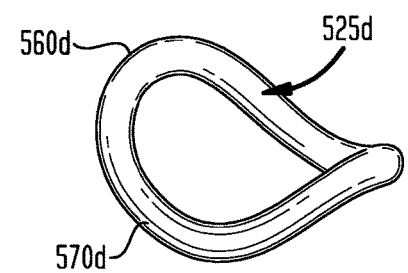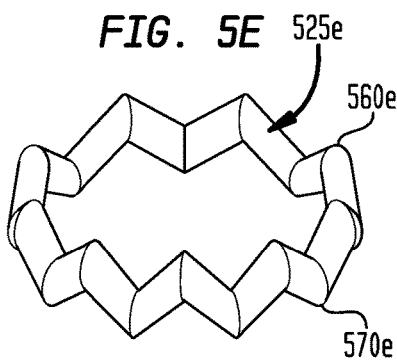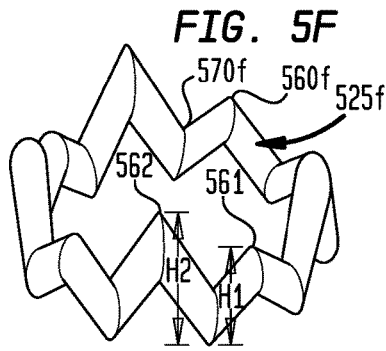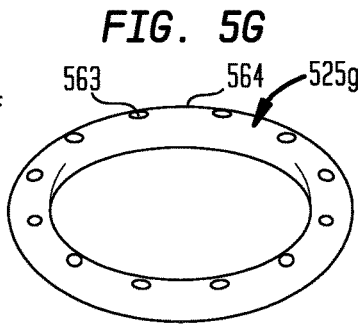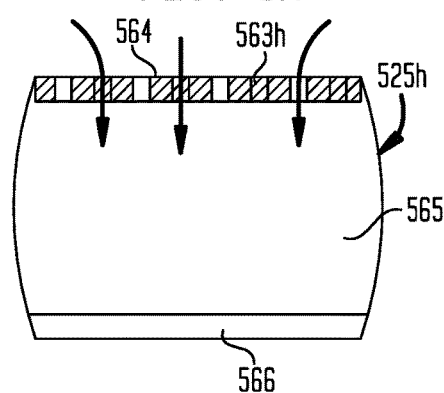

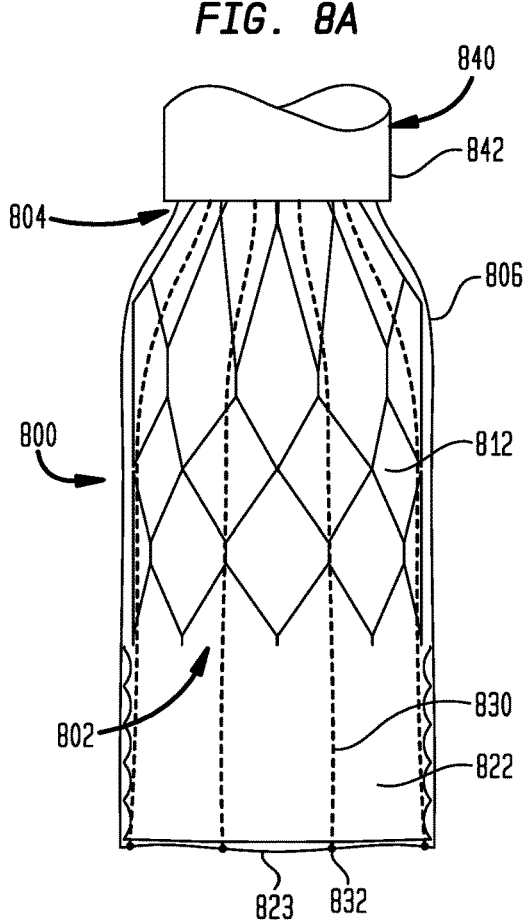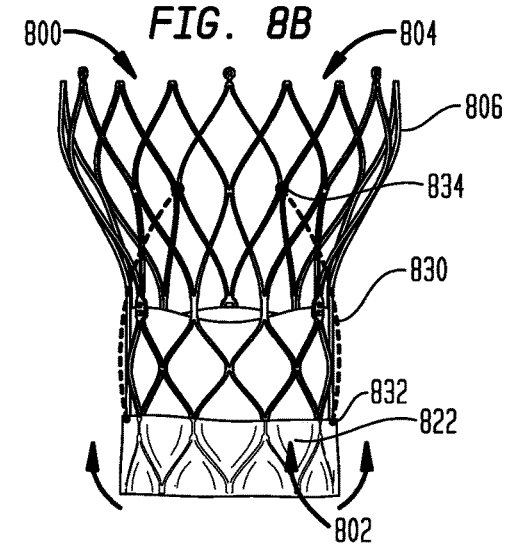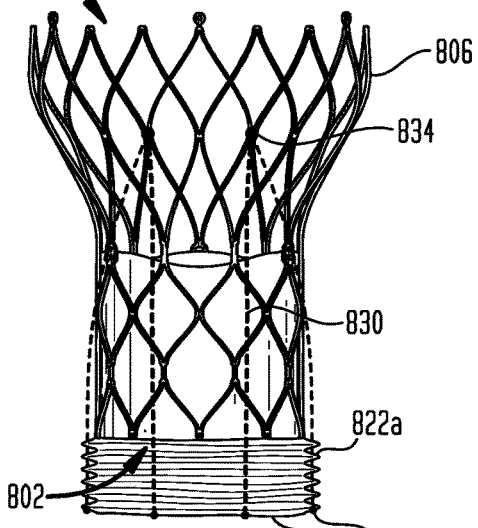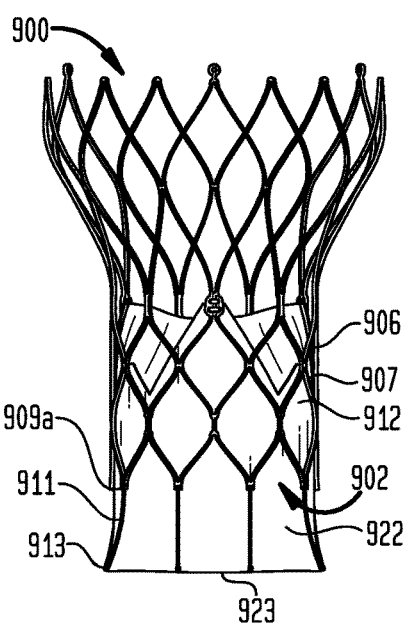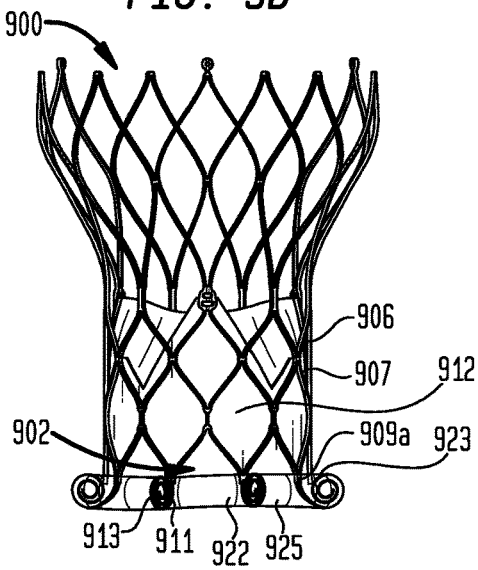

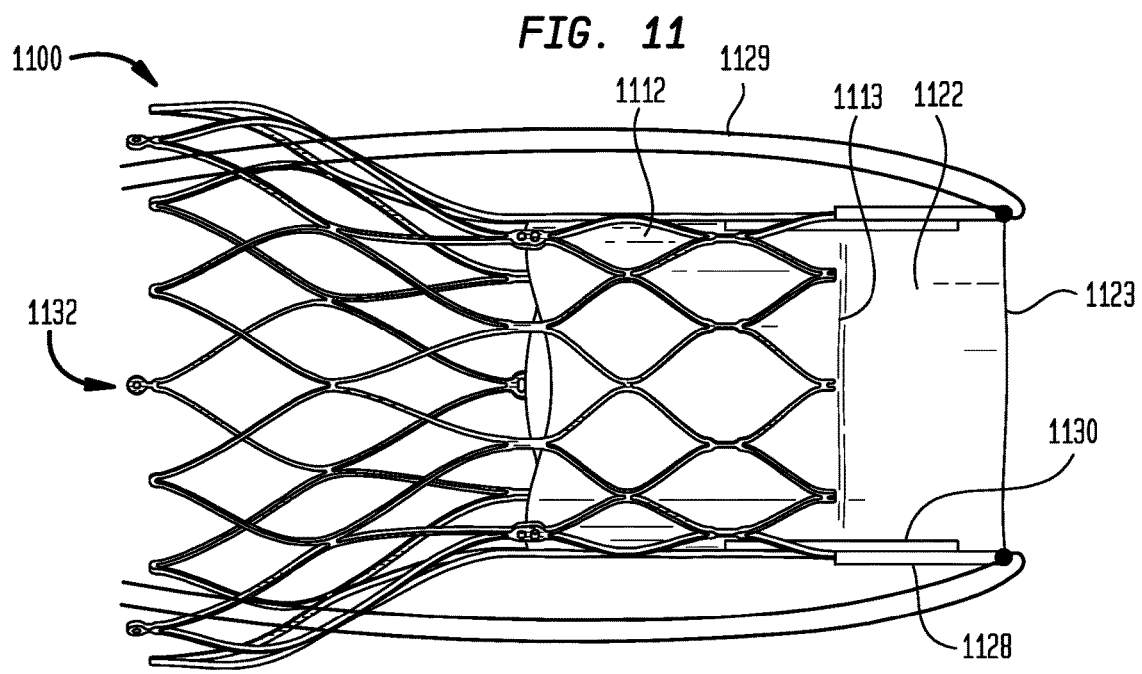
FIG. 11
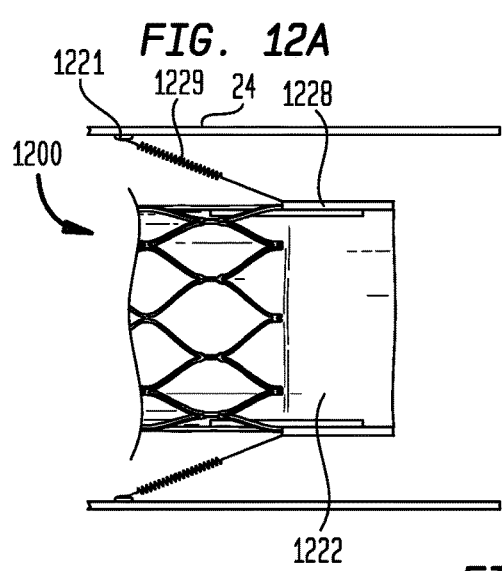
FIG. 12A
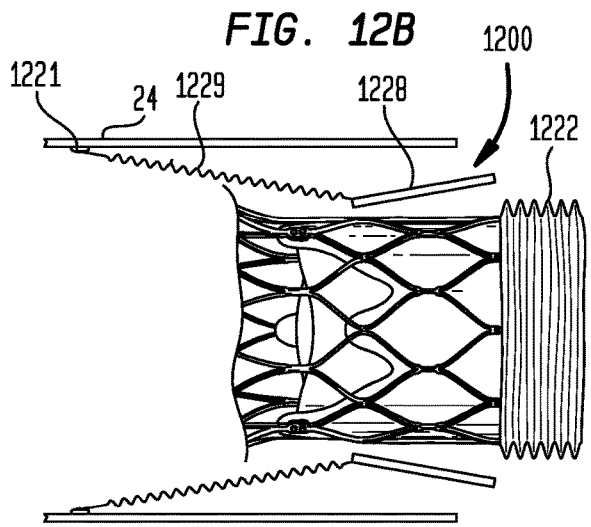
FIG. 12B
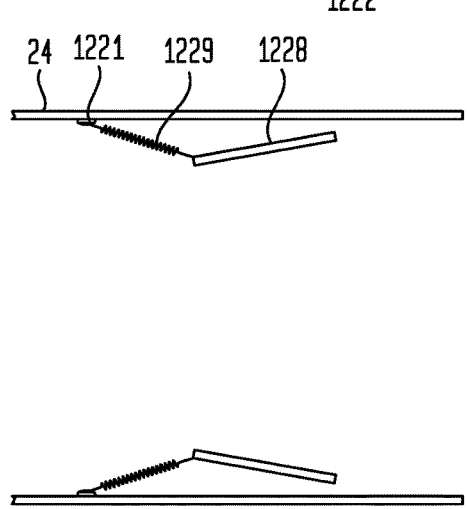
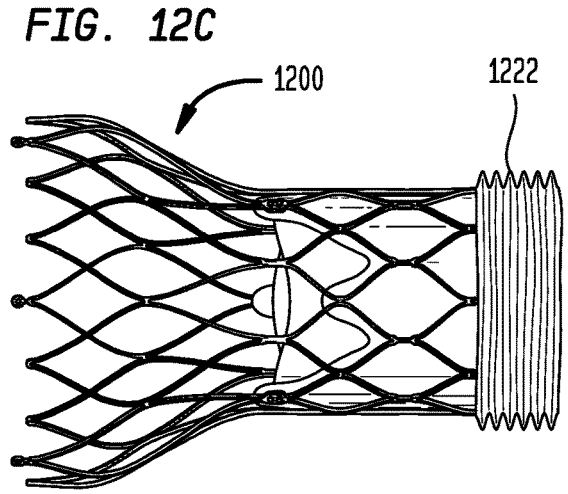
FIG. 12C

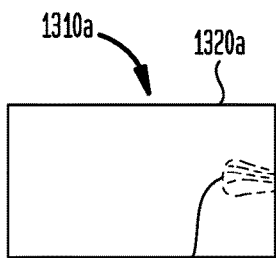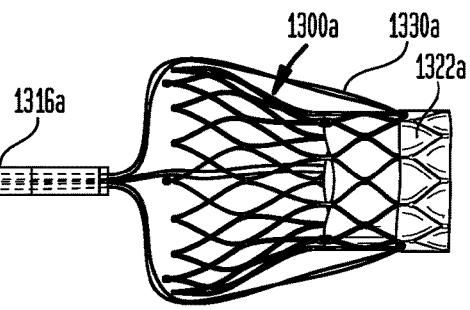
FIG. 13A
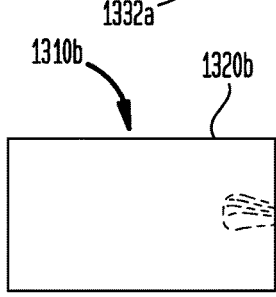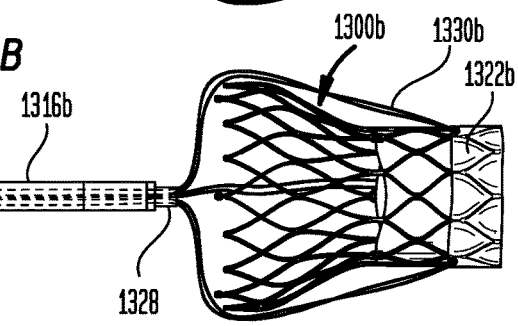
FIG. 13B
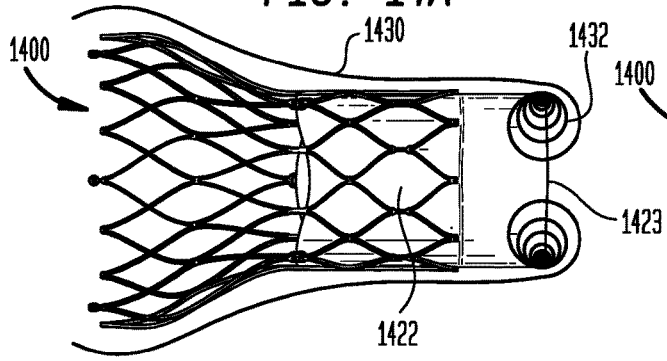
FIG. 14A
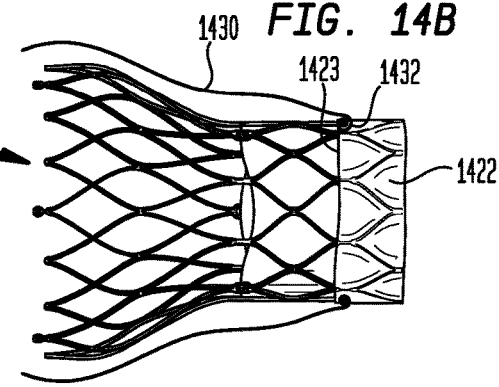
FIG. 14B
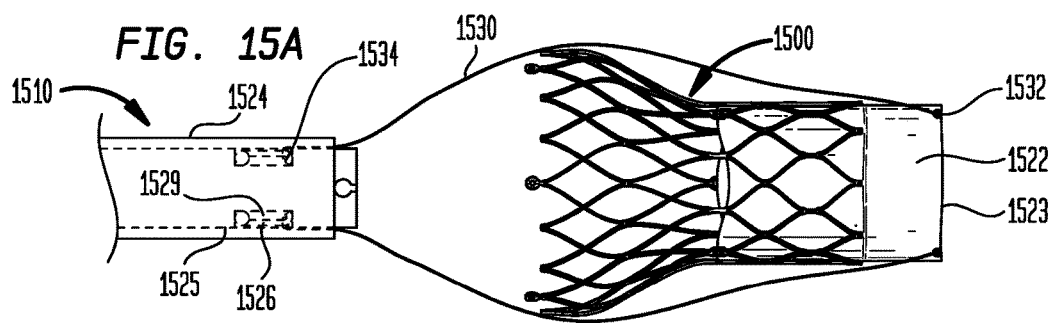
FIG. 15A
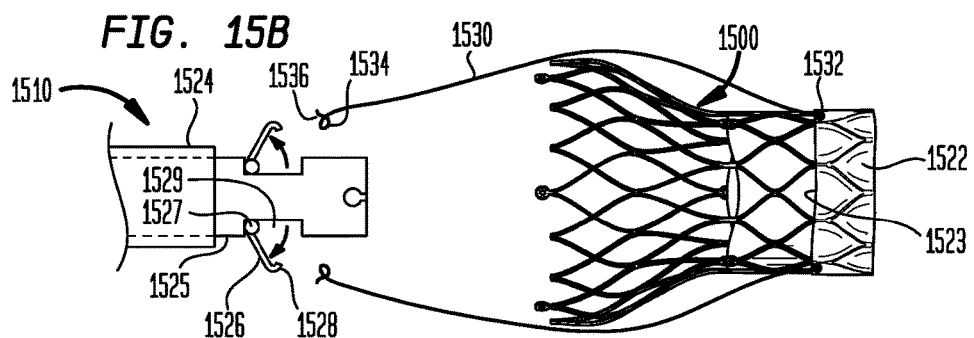
FIG. 15B

PARAVALVULAR SEALING VIA EXTENDED CUFF MECHANISMS

CROSS-REFERENCE TO RELATED APPLICATIONS

This application is a continuation of U.S. application Ser. No. 15/128,909, filed Sep. 23, 2016, which is a national phase entry under 35 U.S.C. § 371 of International Application No. PCT/US2015/011387 filed Jan. 14, 2015, published in English, which claims the benefit of the filing date of U.S. Provisional Patent Application No. 61/972,831 filed Mar. 31, 2014, the disclosures of which are hereby incorporated herein by reference.

BACKGROUND OF THE INVENTION

The present disclosure relates in general to heart valve replacement and, in particular, to collapsible prosthetic heart valves. More particularly, the present disclosure relates to devices and methods for positioning and sealing collapsible prosthetic heart valves within a native valve annulus.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two common types of stents on which the valve structures are ordinarily mounted: a self-expanding stent or a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, and then expanding a balloon positioned within the valve stent. For self-expanding valves, on the other hand, the stent automatically expands as the sheath covering the valve is withdrawn.

BRIEF SUMMARY OF THE INVENTION

Described herein is a prosthetic heart valve configured to be expanded proximate a native valve of a patient. The prosthetic heart valve may include a collapsible and expandable stent having a proximal end, a distal end, an annulus section adjacent the proximal end, and a plurality of cells connected to one another in a plurality of annular rows around the stent, a cuff attached to the annulus section of the stent and defining an outward-facing surface, a plurality of prosthetic valve leaflets attached to the cuff, and a sealing member attached to the cuff and extending from a proximal end of the cuff to a free edge. The stent may have a flow direction extending from the proximal end of the stent toward the distal end of the stent. The sealing member may be movable between an extended condition in which the free edge is located proximally of the proximal end of the stent, and an inverted condition in which the free edge is located distally of the proximal end of the stent and a first surface of the sealing member confronts the outward-facing surface of the cuff.

Also described herein is another prosthetic heart valve configured to be expanded proximate a native valve of a patient. The prosthetic heart valve may include a collapsible and expandable stent having a proximal end, a distal end, an annulus section adjacent the proximal end, and a plurality of cells connected to one another in a plurality of annular rows around the stent, a cuff attached to the annulus section of the stent and defining an outward-facing surface, a plurality of prosthetic valve leaflets attached to the cuff, and a sealing member attached to the cuff and extending from a proximal end of the cuff to a free edge. The stent may have a flow direction extending from the proximal end of the stent toward the distal end of the stent. The sealing member may be movable between an extended condition in which the free edge is located a first distance proximally of the proximal end of the stent, and a compressed condition in which the free edge is located a second distance proximally of the proximal end of the stent.

Also described herein is a method of expanding a prosthetic heart valve proximate a native valve of a patient. The prosthetic heart valve may include a stent having proximal and distal ends, a cuff attached to the stent, and a sealing member extending from a proximal end of the cuff to a free edge.

The method may include collapsing the prosthetic heart valve into a delivery device such that the sealing member is in an extended condition in which the free edge is located proximally of the proximal end of the stent, inserting the delivery device into a patient, advancing the delivery device proximate an annulus of the native valve, partially expanding the prosthetic heart valve in a selected position proximate the native valve, moving the sealing member from the extended condition to an inverted condition in which the free edge is located distally of the proximal end of the stent, and fully expanding the prosthetic heart valve.

Also described herein is a system including a delivery device and a prosthetic heart valve. The delivery device may include an operating handle and a catheter assembly. The catheter assembly may include a first shaft around which a compartment is defined, the first shaft being operatively connected to the operating handle, and a distal sheath at least partially surrounding the first shaft, the distal sheath being moveable between a closed condition covering the compartment and an open condition uncovering the compartment for deployment of the valve.

The prosthetic heart valve may be mounted in the compartment. The prosthetic valve may include a collapsible and expandable stent, a cuff, and a sealing member attached to the cuff. The stent may have a proximal end, a distal end, and an annulus section adjacent the proximal end, the stent having a flow direction extending from the proximal end toward the distal end. The cuff may be attached to the annulus section of the stent and may define an outward-facing surface.

The sealing member may extend from a proximal end of the cuff to a free edge, the sealing member being movable between an extended condition in which the free edge is located at a first location proximally of the proximal end of the stent, and a use condition in which the free edge is located at a second location distally of the first location and a first surface of the sealing member confronts the outward-facing surface of the cuff. The sealing member may have an energy storage element with a bias to move the sealing member toward the use condition. The catheter assembly may have a restraining member removably coupled to the sealing member to hold the sealing member in the extended condition against the bias of the energy storage element.

Also described herein is a system including a delivery device and a prosthetic heart valve. The delivery device may include an operating handle and a catheter assembly. The catheter assembly may include a first shaft around which a compartment is defined, the first shaft being operatively connected to the operating handle, and a distal sheath at least partially surrounding the first shaft, the distal sheath being moveable between a closed condition overing the compartment and an open condition uncovering the compartment for deployment of the valve.

The prosthetic heart valve may be mounted in the compartment. The prosthetic valve may include a collapsible and expandable stent, a cuff, and a sealing member attached to the cuff. The stent may have a proximal end, a distal end, and an annulus section adjacent the proximal end, the stent having a flow direction extending from the proximal end toward the distal end. The cuff may be attached to the annulus section of the stent and may define an outward-facing surface.

The sealing member may extend from a proximal end of the cuff to a free edge, the sealing member being movable between an extended condition in which the free edge is located at a first location proximally of the proximal end of the stent, and a use condition in which the free edge is located at a second location distally of the first location and a first surface of the sealing member confronts the outward-facing surface of the cuff. The catheter assembly may have an actuating filament having a portion removably coupled to the sealing member and configured to move the sealing member from the extended condition to the use condition when the portion of the actuating filament is moved toward the operating handle.

Also described herein is a system including a delivery device and a prosthetic heart valve. The delivery device may include an operating handle and a catheter assembly. The catheter assembly may include a first shaft around which a compartment is defined, the first shaft being operatively connected to the operating handle, and a distal sheath at least partially surrounding the first shaft, the distal sheath being moveable between a closed condition covering the compartment and an open condition uncovering the compartment for deployment of the valve.

The prosthetic heart valve may be mounted in the compartment. The prosthetic valve may include a collapsible and expandable stent, a cuff, and a sealing member attached to the cuff. The stent may have a proximal end, a distal end, and an annulus section adjacent the proximal end, the stent having a flow direction extending from the proximal end toward the distal end. The cuff may be attached to the annulus section of the stent and may define an outward-facing surface.

The sealing member may extend from a proximal end of the cuff to a free edge, the sealing member being movable between an extended condition in which the free edge is located at a first location proximally of the proximal end of the stent, and a use condition in which the free edge is located at a second location distally of the first location and a first surface of the sealing member confronts the outward-facing surface of the cuff. The catheter assembly may have an actuating filament removably coupled to a retaining element of the catheter assembly and configured to move the sealing member from the extended condition to the use condition when a portion of the actuating filament is moved toward the operating handle.

Also described herein is a system including a delivery device and a prosthetic heart valve. The delivery device may include an operating handle and a catheter assembly. The catheter assembly may include a first shaft around which a compartment is defined, the first shaft being operatively connected to the operating handle, and a distal sheath at least partially surrounding the first shaft, the distal sheath being moveable between a closed condition covering the compartment and an open condition uncovering the compartment for deployment of the valve.

The prosthetic heart valve may be mounted in the compartment. The prosthetic valve may include a collapsible and expandable stent, a cuff, a sealing member attached to the cuff, an expandable anchor portion having a generally cylindrical shape, and an actuating filament. The stent may have a proximal end, a distal end, and an annulus section adjacent the proximal end, the stent having a flow direction extending from the proximal end toward the distal end. The cuff may be attached to the annulus section of the stent and may define an outward-facing surface.

The sealing member may extend from a proximal end of the cuff to a free edge, the sealing member being movable between an extended condition in which the free edge is located at a first location proximally of the proximal end of the stent, and a use condition in which the free edge is located at a second location distally of the first location and a first surface of the sealing member confronts the outward-facing surface of the cuff. The actuating filament may extend between the free edge of the sealing member and the expandable anchor portion, the actuating filament configured to move the sealing member from the extended condition to the use condition when the expandable anchor portion is moved toward the operating handle.

Also described herein is a method of expanding a prosthetic heart valve proximate a native valve of a patient. The prosthetic heart valve may include a stent having proximal and distal ends, a cuff attached to the stent, and a sealing member extending from a proximal end of the cuff to a free edge.

The method may include collapsing the prosthetic heart valve into a delivery device such that the sealing member is in an extended condition in which the free edge is located proximally of the proximal end of the stent, inserting the delivery device into a patient, advancing the delivery device proximate an annulus of the native valve, expanding the prosthetic heart valve from a first diameter to a second diameter greater than the first diameter in a selected position proximate the native valve, and moving the sealing member from the extended condition to a use condition in which the free edge is located at a second location distally of the first location.

BRIEF DESCRIPTION OF THE DRAWINGS

Various embodiments of heart valves are disclosed herein with reference to the drawings, wherein:

FIG. 3A is a side view of an embodiment of a prosthetic heart valve having a sealing member for filling irregularities between the heart valve and the native valve annulus in accordance with the present disclosure, with the sealing member in an extended condition;

FIG. 3B is a side view of the prosthetic heart valve of FIG. 3A, with the sealing member in an inverted condition;

FIG. 3C is a highly schematic perspective view of the cuff and sealing member of FIG. 3B;

FIG. 5A is a side view of another embodiment of a prosthetic heart valve having a sealing ring for filling irregularities between the heart valve and the native valve annulus in accordance with the present disclosure, with the sealing ring in the inverted condition;

FIG. 5B is a highly schematic perspective view of the prosthetic heart valve of FIG. 5A, with the sealing ring in the extended condition;

FIG. 5C is a side view of another embodiment of a prosthetic heart valve having two sealing rings for filling irregularities between the heart valve and the native valve annulus;

FIGS. 5D-5G are highly schematic perspective views of alternative sealing ring embodiments that can be used with the stent, cuff, sealing member, and leaflets of the embodiment of FIGS. 5A-5C;

FIG. 5H is a highly schematic cross-sectional view of an alternative sealing ring feature that can be used with any of the sealing ring embodiments of FIGS. 5A-5G;

FIG. 8A is a highly schematic side view of an embodiment of a prosthetic heart valve having a sealing member for filling irregularities between the heart valve and the native valve annulus in accordance with the present disclosure, with the sealing member in an extended condition;

FIG. 8B is a highly schematic side view of the prosthetic heart valve of FIG. 8A, with the sealing member in an inverted condition;

FIG. 8C is a highly schematic side view of the prosthetic heart valve of FIG. 8A, with the sealing member in a contracted condition;

FIG. 9A is a partial highly schematic side view of an embodiment of a prosthetic heart valve having a sealing member for filling irregularities between the heart valve and the native valve annulus in accordance with the present disclosure, with the sealing member in an extended condition;

FIG. 9B is a partial highly schematic side view of the prosthetic heart valve of FIG. 9A, with the sealing member in a rolled condition;

FIG. 11 is a highly schematic side view of an embodiment of a prosthetic heart valve having a sealing member for filling irregularities between the heart valve and the native valve annulus in accordance with the present disclosure, with the sealing member in an extended condition;

FIG. 12A is a highly schematic cross-sectional view of an embodiment of a prosthetic heart valve having a sealing member for filling irregularities between the heart valve and the native valve annulus in accordance with the present disclosure, with the sealing member in an extended condition, shown in the distal end of a delivery device;

FIG. 12B is a highly schematic cross-sectional view of the prosthetic heart valve and distal end of the delivery device of FIG. 12A, with the sealing member in a contracted condition;

FIG. 12C is a highly schematic cross-sectional view of the prosthetic heart valve of FIG. 12A, with the prosthetic heart valve released from the delivery device;

FIG. 13A is a highly schematic cross-sectional view of an embodiment of a prosthetic heart valve having a sealing member for filling irregularities between the heart valve and the native valve annulus in accordance with the present disclosure, with the sealing member in an inverted condition, shown coupled to the distal end of a delivery device;

FIG. 13B is a highly schematic cross-sectional view of a variant of the prosthetic heart valve and distal end of the delivery device of FIG. 13A, with the sealing member in an inverted condition;

FIG. 14A is a highly schematic cross-sectional view of an embodiment of a prosthetic heart valve having a sealing member for filling irregularities between the heart valve and the native valve annulus in accordance with the present disclosure, with the sealing member in an extended condition;

FIG. 14B is a highly schematic cross-sectional view of the prosthetic heart valve of FIG. 14A, with the sealing member in an inverted condition;

FIG. 15A is a highly schematic cross-sectional view of an embodiment of a prosthetic heart valve having a sealing member for filling irregularities between the heart valve and the native valve annulus in accordance with the present disclosure, with the sealing member in an extended condition, shown coupled to the distal end of a delivery device;

FIG. 15B is a highly schematic cross-sectional view of the prosthetic heart valve and distal end of the delivery device of FIG. 15A, with the sealing member in an inverted condition;

Figure 1:
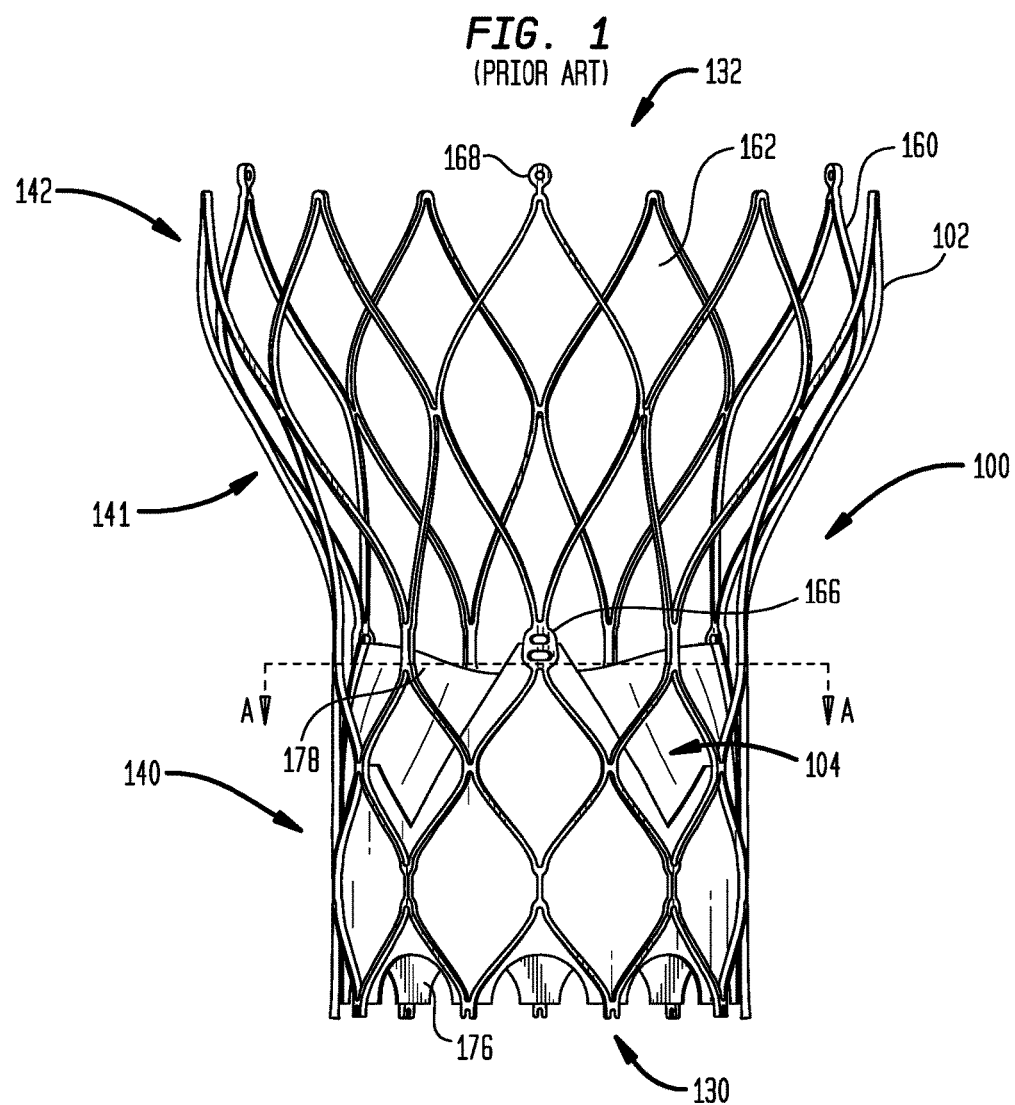
FIG. 1 is a side elevational view of a conventional prosthetic heart valve.

Various embodiments of the present disclosure will now be described with reference to the appended drawings. It is to be appreciated that these drawings depict only some embodiments of the disclosure and are therefore not to be considered limiting of its scope.

DETAILED DESCRIPTION

With conventional self-expanding valves, clinical success of the valve is dependent on accurate deployment and anchoring. Inaccurate deployment and anchoring of the valve increases risks, such as those associated with valve migration. Inaccurate deployment and anchoring may also result in the leakage of blood between the implanted heart valve and the native valve annulus, commonly referred to as perivalvular leakage (also known as "paravalvular leakage"). In aortic valves, this leakage enables blood to flow from the aorta back into the left ventricle, reducing cardiac efficiency and putting a greater strain on the heart muscle. Additionally, calcification of the aortic valve may affect performance and the interaction between the implanted valve and the calcified tissue is believed to be relevant to leakage, as will be outlined below.

Moreover, anatomical variations from one patient to another may cause a fully deployed heart valve to function improperly, requiring removal of the valve from the patient. Removing a fully deployed heart valve increases the length of the deployment procedure as well as the risk of infection and/or damage to heart tissue. Thus, methods and devices are desirable that reduce the need to remove a prosthetic heart valve from a patient. Methods and devices are also desirable that reduce the likelihood of perivalvular leakage due to gaps between the implanted heart valve and patient tissue.

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. When used in connection with devices for delivering a prosthetic heart valve or other medical device into a patient, the terms "proximal" and "distal" are to be taken as relative to the user of the delivery devices. "Proximal" is to be understood as relatively close to the user, and "distal" is to be understood as relatively farther away from the user. Also as used herein, the terms "generally," "substantially," "approximately," and "about" are intended to mean that slight deviations from absolute are included within the scope of the term so modified.

When used to indicate relative locations within the aortic annulus, the aortic root, and the ascending aorta of a patient, the terms "above" and "below" are to be taken as relative to the juncture between the aortic annulus and the left ventricle. "Above" is to be understood as relatively farther from the left ventricle, and "below" is to be understood as relatively closer to the left ventricle.

When used to indicate relative locations within the prosthetic heart valve, the terms "longitudinal" and "vertical" are to be taken as the direction of the axis extending between the proximal end and the distal end of the heart valve, along the direction of intended blood flow; the term "flow direction" is to be taken as the direction from the proximal end to the distal end of the heart valve, along the direction of intended blood flow; and the terms "above," "below," "high," and "low" are to be taken as relative to the proximal end of the prosthetic heart valve. "Above" and "high" are to be understood as relatively farther from the proximal end of the heart valve in the direction of intended blood flow, and "below" and "low" are to be understood as relatively closer to the proximal end of the stent in the direction of intended blood flow. When used to indicate relative locations within the prosthetic heart valve, the term "circumferential" is to be taken as the direction of rotation about the longitudinal axis of the stent.

The sealing portions of the present disclosure may be used in connection with collapsible prosthetic heart valves. FIG. 1 shows one such collapsible stent-supported prosthetic heart valve 100 including stent 102 and valve assembly 104 as is known in the art. The prosthetic heart valve 100 is designed to replace a native tricuspid valve of a patient, such as a native aortic valve. It should be noted that while the embodiments herein are described predominantly in connection with their use with a prosthetic aortic valve and a stent having a shape as illustrated in FIG. 1, the valve could be a bicuspid valve, such as the mitral valve, and the stent could have different shapes, such as a flared or conical annulus section, a less-bulbous aortic section, and the like, and a differently shaped transition section.

Stent 102 may be formed from biocompatible materials that are capable of self-expansion, such as, for example, shape memory alloys, such as the nickel-titanium alloy known as "Nitinol" or other suitable metals or polymers. Stent 102 extends from proximal or annulus end 130 to distal or aortic end 132, and includes annulus section 140 adjacent proximal end 130, transition section 141, and aortic section 142 adjacent distal end 132. Annulus section 140 has a relatively small cross-section in the expanded condition, while aortic section 142 has a relatively large cross-section in the expanded condition. Annulus section 140 may be in the form of a cylinder having a substantially constant diameter along its length. Transition section 141 may taper outwardly from annulus section 140 to aortic section 142.

Each of the sections of stent 102 includes a plurality of struts 160 forming cells 162 connected to one another in one or more annular rows around the stent. For example, as shown in FIG. 1, annulus section 140 may have two annular rows of complete cells 162 and aortic section 142 and transition section 141 may each have one or more annular rows of partial cells 162. Cells 162 in aortic section 142 may be larger than cells 162 in annulus section 140. The larger cells in aortic section 142 better enable prosthetic valve 100 to be positioned in the native valve annulus without the stent structure interfering with blood flow to the coronary arteries.

Stent 102 may include one or more retaining elements 168 at distal end 132 thereof, retaining elements 168 being sized and shaped to cooperate with female retaining structures (not shown) provided on the deployment device. The engagement of retaining elements 168 with the female retaining structures on the deployment device helps maintain prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and the heart valve deployed.

Prosthetic heart valve 100 includes valve assembly 104, preferably positioned in annulus section 140 of stent 102 and secured to the stent. Valve assembly 104 includes cuff 176 and a plurality of leaflets 178 that collectively function as a one-way valve by coapting with one another. As a prosthetic aortic valve, prosthetic heart valve 100 has three leaflets 178. However, it will be appreciated that other prosthetic heart valves with which the sealing portions of the present disclosure may be used may have a greater or lesser number of leaflets 178.

Although cuff 176 is shown in FIG. 1 as being disposed on the luminal or inner surface of annulus section 140, it is contemplated that cuff 176 may be disposed on the abluminal or outer surface of annulus section 140 or may cover all or part of either or both of the luminal and abluminal surfaces. Both cuff 176 and leaflets 178 may be wholly or partly formed of any suitable biological material or polymer such as, for example, polytetrafluoroethylene (PTFE), polyvinyl alcohol (PVA), ultra-high molecular weight polyethylene (UHMWPE), silicone, urethane, and the like.

Leaflets 178 may be attached along their belly portions to cells 162 of stent 102, with the commissure between adjacent leaflets 178 attached to commissure features 166. As can be seen in FIG. 1, each commissure feature 166 may lie at the intersection of four cells 162, two of the cells being adjacent one another in the same annular row, and the other two cells being in different annular rows and lying in end-to-end relationship. Preferably, commissure features 166 are positioned entirely within annulus section 140 or at the juncture of annulus section 140 and transition section 141. Commissure features 166 may include one or more eyelets that facilitate the suturing of the leaflet commissure to stent 102.

Prosthetic heart valve 100 may be used to replace a native aortic valve, a surgical heart valve, a heart valve that has undergone a surgical procedure, or any other valve that is desired to be replaced. Prosthetic heart valve 100 may be delivered to the desired site (e.g., near or proximate a native annulus, near or proximate an annuloplasty ring or other repair device) using any suitable delivery device.

During delivery, prosthetic heart valve 100 is disposed inside the delivery device in the collapsed condition. The delivery device may be introduced into a patient using a transfemoral, transapical, transseptal, transradial, transsubclavian, transaortic or any other percutaneous approach. Once the delivery device has reached the target site, the user may deploy prosthetic heart valve 100. Upon deployment, prosthetic heart valve 100 expands so that annulus section 140 is in secure engagement within the native annulus (or in engagement with an annuloplasty ring or other repair device). When prosthetic heart valve 100 is properly positioned, it works as a one-way valve, allowing blood to flow in an antegrade or flow direction, and preventing blood from flowing in the opposite direction.

Problems may be encountered when implanting prosthetic heart valve 100. For example, in certain procedures, collapsible valves may be implanted in a native valve annulus without first resecting the native valve leaflets. The collapsible valves may have clinical issues because of the nature of the stenotic leaflets that are left in place. Additionally, patients with uneven calcification, bi-cuspid aortic valve disease, and/or valve insufficiency cannot be treated well, if at all, with the current collapsible valve designs.

The reliance on unevenly-calcified leaflets for proper valve placement and seating could lead to several problems, such as perivalvular leakage ("PV leak"), which can have adverse clinical outcomes. To reduce these adverse events, the optimal valve would anchor adequately and seal without the need for excessive radial force that could harm nearby anatomy and physiology.

PV leak may also be caused by the implantation of a valve having an expanded diameter that is too small relative to the native aortic annulus diameter, a prosthetic valve that is deployed in a tilted orientation relative to the native aortic annulus (such that the longitudinal axis of the valve and the native aortic annulus are misaligned), lack of full radial expansion of the valve due to the stent catching on calcific nodules in the native aortic annulus, and placing the valve at a non-optimal longitudinal position relative to the native aortic annulus (either too high or too low along the central axis of the native aortic annulus).

Figure 2A:
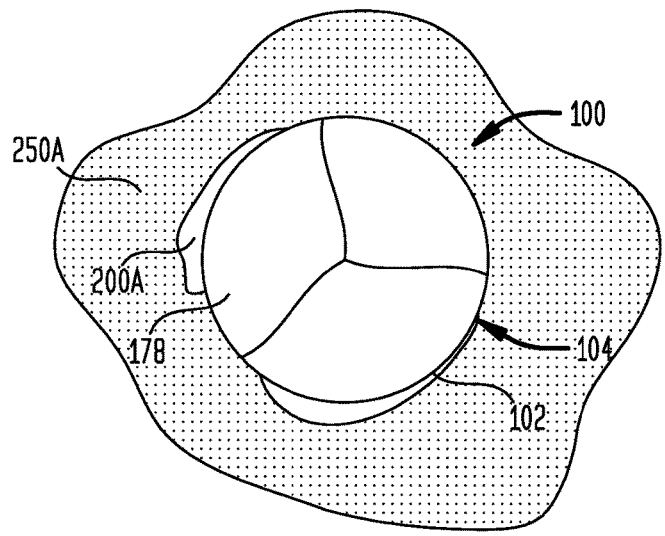
FIG. 2A is a highly schematic cross-sectional view taken along line A-A of FIG. 1 and showing the prosthetic heart valve disposed within a native valve annulus.

FIG. 2A is a highly schematic cross-sectional illustration of prosthetic heart valve 100 disposed within native valve annulus 250A. As seen in the figure, valve assembly 104 has a substantially circular cross-section which is disposed within the non-circular native valve annulus 250A. At certain locations around the perimeter of heart valve 100, gaps 200A form between heart valve 100 and native valve annulus 250A. Blood flowing through these gaps and past valve assembly 104 of prosthetic heart valve 100 can cause regurgitation and other inefficiencies which reduce cardiac performance. Such improper fitment may be due to suboptimal native valve annulus geometry due, for example, to calcification of native valve annulus 250A or to unresected native leaflets.

Figure 2B:
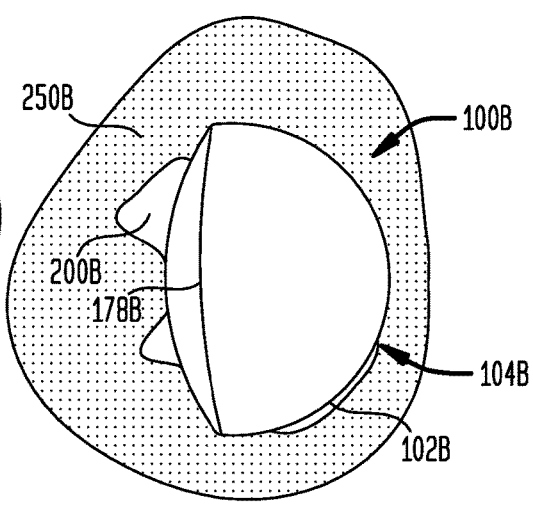
FIG. 2B is a highly schematic cross-sectional view showing a prosthetic mitral valve disposed within a native valve annulus.

FIG. 2B is a similar cross-sectional illustration of prosthetic mitral valve 100B disposed within native valve annulus 250B. As seen in the figure, valve assembly 104B has a substantially D-shaped cross-section that is disposed within irregularly-shaped annulus 250B. At certain locations around the perimeter of heart valve 100B, gaps 200B form between heart valve 100B and native valve annulus 250B. Regurgitation and other inefficiencies may thus result after deployment of a prosthetic mitral valve. Though the following examples show aortic valves, it will be understood that the present devices and methods may be equally applicable to mitral and other heart valves.

FIGS. 3A-3C illustrate prosthetic heart valve 300 in accordance with an embodiment of the disclosure. As can be seen in FIG. 3A, prosthetic heart valve 300 extends between proximal end 302 and distal end 304, and may generally include stent 306 formed of a plurality of struts 307, and valve assembly 308 having a plurality of leaflets 310 and cuff 312.

Valve assembly 308 includes a generally cylindrical sealing member 322 that extends proximally from proximal end 313 of cuff 312. The sealing member 322 may have smooth surfaces, rough or textured surfaces, or a combination of smooth surfaces with a rough or textured surface on one or more surfaces or surface portions to promote tissue ingrowth, which may improve sealing between the sealing member and the native patient anatomy. In FIG. 3A, sealing member 322 is shown in an extended condition. In some examples, sealing member 322 in its extended condition may extend between about 8 mm and about 16 mm proximally of proximal end 302 of stent 306 to free edge 323.

One or more removable sutures 330 may extend through respective apertures in sealing member 322 adjacent its free edge 323, and the free ends of each suture may extend proximally through a delivery device so as to be accessible to a user. In one example, one or more sutures 330 may be pulled by the user at the proximal end of the delivery device to move sealing member 322 from the extended condition (FIG. 3A) to an inverted condition (FIG. 3B), as will be described in greater detail below with reference to FIGS. 4E and 4F. In a variation, sutures 330 may be replaced with other filamentary elements that may extend between free edge 323 and the proximal end of the delivery device, such as at least one polymer wire, braided metal wire, Nitinol wire, cord, ribbon, or any other connecting member that may be used to pull sealing member 322 to an inverted condition (FIGS. 3B and 3C). In another variation (e.g., FIGS. 10A-10C), one or more sutures 330 or other members may be pulled automatically during deployment of prosthetic heart valve 300 from a delivery device. A description of this variation is set forth in detail below.

In FIGS. 3B and 3C, sealing member 322 is shown in the inverted condition in which the sealing member may be annularly disposed around the abluminal surface of cuff 312 at proximal end 302 of stent 306, such that a surface 324 of the sealing member that was facing radially outward from the longitudinal axis of stent 306 in FIG. 3A confronts the abluminal surface of the cuff. In other words, sealing member 322 is inverted and folded proximally over proximal end 302 of stent 306. Proximal end 313 of cuff 312 where the cuff and sealing member 322 meet is disposed at the proximalmost junctions 309a of the stent, and free edge 323 of sealing member 322 is disposed at or near upper junctions 309b of the proximalmost struts 307 of stent 306.

In the inverted condition, sealing member 322 may have a radius larger than that of the proximal end 302 of stent 306, the larger radius of the sealing member being capable of filling gaps between prosthetic heart valve 300 and the native valve annulus and/or blocking blood flow through same.

To improve the capability of sealing member 322 to fill gaps between prosthetic heart valve 300 and the native valve annulus, sealing member 322, and all of the other sealing members and rings described herein, may have an outward spring bias. Such an outward spring bias is preferably small enough that the sealing member may expand to different radial distances at some locations along the circumference of the sealing member than at other locations. The sealing member may expand a greater radial distance where there is minimal radial force applied to the sealing member from the native anatomy (i.e., at locations at which voids or gaps between stent 306 and the native anatomy are present, such as gaps 200A shown in FIG. 2A). The sealing member may expand a lesser radial distance where there is greater radial force applied to the sealing member from the native anatomy (i.e., at locations at which there are no such voids or gaps).

Sealing member 322 may be formed of the same material as cuff 312 and may be formed integrally therewith from a single piece of material. Alternatively, sealing member 322 may be formed of the same material or a different material than cuff 312 that is sutured, glued or otherwise affixed to proximal end 313 of the cuff. In one example, sealing member 322 may be made of a thin tubular fabric material. In other examples, sealing member 322 may include thin porcine pericardial tissue between about 0.005 inches (127 µm) and about 0.007 inches (177.8 µm) in thickness, or ultra-high-molecular-weight polyethylene (UHMWPE) or polyethylene terephthalate (PET) fabric between about 0.003 inches (76.2 µm) and about 0.005 inches (127 µm) in thickness.

Alternatively, a variety of other materials may be used, including bovine tissue (e.g., glycerol impregnated or freeze dried), tissue with support structures therein, wire mesh, radiopaque wire, fabric, braided or woven fabric (e.g., polytetrafluoroethylene (PTFE), PET, or UHMWPE), fabric coated with PTFE or collagen, or a multi-layered composite of one or more of the aforementioned materials (e.g., a fabric and tissue composite). Any of the sealing rings or sealing members disclosed herein may be made of any one of the aforementioned materials or a combination thereof.

Sealing member 322 may be at least partially radiopaque, i.e., the sealing member may include one or more materials having enhanced visibility to a user under fluoroscopy. For example, sealing member 322 may be a fabric or wire mesh material having radiopaque fibers or may be comprised entirely of radiopaque fibers. Sealing member 322 may include radiopaque marker beads, a thin radiopaque wire, radiopaque paint, or may be impregnated with a radiopaque material such as silver, iodine, barium, platinum, or the like, such as by soaking the sealing member in a liquid including one or more of these chemicals. Any of the sealing members or sealing rings disclosed herein may include any one of the aforementioned radiopaque materials or a combination thereof.

Although the sutures 330 are described herein as extending through apertures in sealing member 322 adjacent its free edge 323, the apertures need not be formed in the sealing member before the sutures are attached to the sealing member. The invention contemplates threading the sutures 330 directly through the material of sealing member 322. For example, in an embodiment in which sealing member 322 is made of a fabric, sutures 330 may be threaded through gaps extending between fibers of the fabric, such that no additional apertures are created by the action of threading the sutures through the sealing member.

Figure 4A:
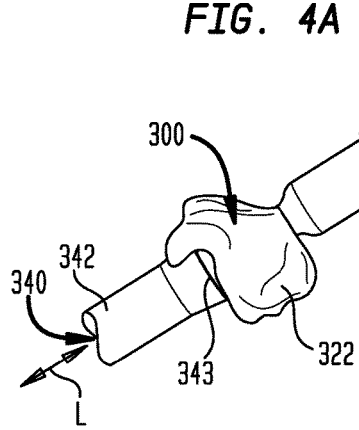
FIGS. 4A-4F are perspective views showing stages of deployment of the prosthetic heart valve of FIG. 3A.
Figure 4B:
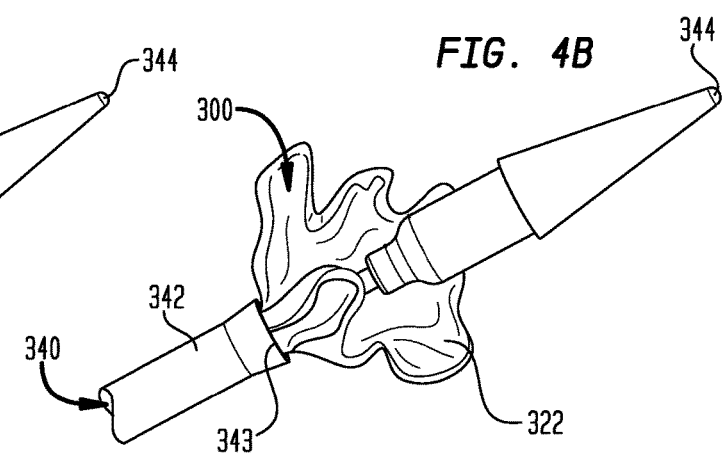

A method of inverting sealing member 322 during release of prosthetic heart valve 300 from distal sheath 342 of delivery device 340 (FIG. 4A) will now be described. Referring to FIG. 4A, prosthetic heart valve 300 is disposed in a compartment defined within distal sheath 342 of delivery device 340, with the proximal end of the stent disposed adjacent distal tip 344 of the delivery device. In FIG. 4A, the compartment is slightly open, with distal end 343 of distal sheath 342 slightly spaced apart from distal tip 344 in the longitudinal direction L of delivery device 340. As shown in FIG. 4B, distal sheath 342 has been withdrawn proximally in the longitudinal direction L, so that more of sealing member 322 has been uncovered and protrudes radially away from the longitudinal axis of delivery device 340.

Figure 4C:
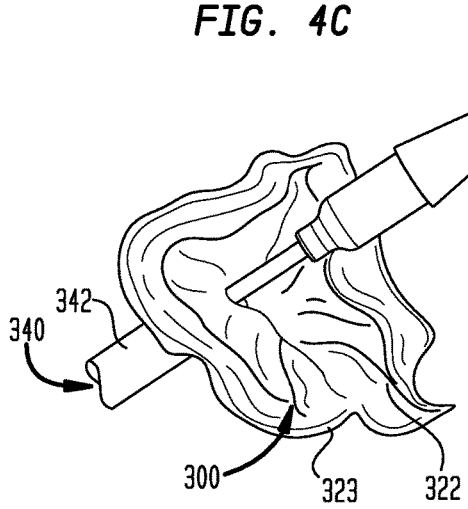
Figure 4D:
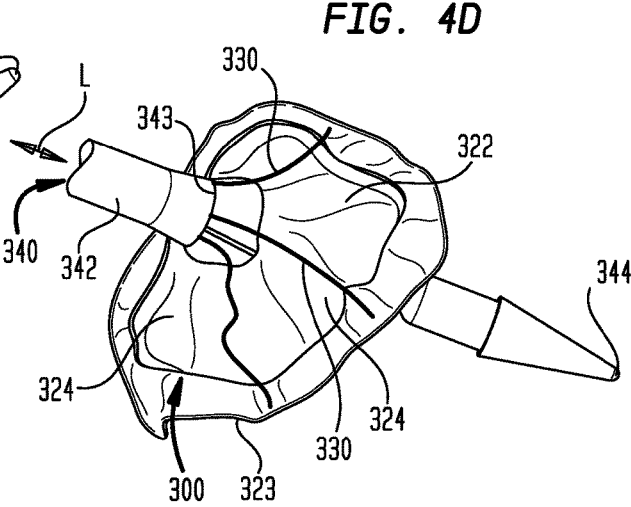

FIGS. 4C and 4D show distal sheath 342 withdrawn further in the proximal direction from distal tip 344, so that the entire sealing member 322 has been uncovered and protrudes further radially away from the longitudinal axis of delivery device 340. Removable sutures 330 can be seen in FIG. 4D extending out of distal sheath 342 and through sealing member 322 at a location adjacent free edge 323.

Figure 4E:
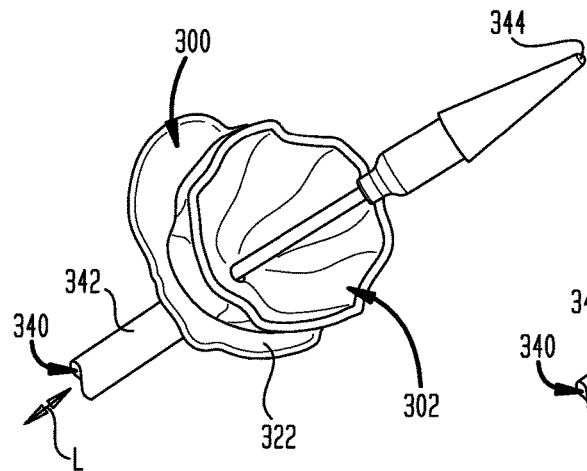

FIG. 4E shows sealing member 322 being partially inverted relative to the extended condition shown in FIG. 4D. A user may begin to invert sealing member 322 by pulling on sutures 330 in the longitudinal direction L toward a proximal end (not shown) of delivery device 340. Sutures 330 may extend from a location adjacent free edge 323 of sealing member 322 to the proximal end of delivery device 340 through a containment tube (not shown) extending within distal sheath 342.

Figure 4F:
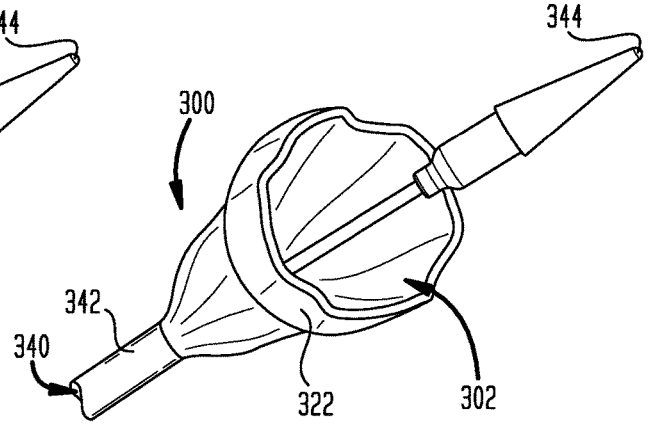

As can be seen in FIG. 4F, distal sheath 342 has been further withdrawn from the compartment, and sealing member 322 has been moved into the inverted condition. The proximal end 302 of stent 306 has been radially expanded, thereby tightening sealing member 322 against the stent and completing the inversion of the sealing member. After sealing member 322 has been inverted, a user may cut sutures 330 at the proximal end of delivery device 340, and may pull one end of each suture until the suture withdraws from the apertures in sealing member 322 and from the delivery device.

In one example, in an embodiment in which sutures 330 are pulled automatically during deployment of prosthetic heart valve 300 from a delivery device, the sutures may remain in a patient with the cuff instead of being removed, which may help sealing member 322 maintain an inverted position under backpressure from blood flowing through the prosthetic heart valve. The backpressure may help pin sealing member 322 between stent 306 and the native anatomy of the patient, thereby anchoring the sealing member in place. In such an example, the sutures may be biodegradable.

Instead of a user cutting sutures 330, the sutures may be released by a delivery device after sealing member 322 has been inverted. In a particular example, the delivery device may include a cutting mechanism that may be actuated by a user after sealing member 322 has been inverted to cut sutures 330 that may be removed from a patient along with the delivery device.

In another embodiment, sutures 330 may extend between sealing member 322 and a portion of a delivery device that may initially retain and later release the sutures from the delivery device. For example, such a portion may include a clip having an initial closed condition in which ends of sutures 330 are retained therein, and after sealing member 322 has been inverted, the clip may be opened by user actuation to release the sutures. In another example, such a portion may include a nitinol wire having an end extending out of a containment tube, the end of the wire having an initial hook-shaped condition (due to shape memory of the wire) in which ends of sutures 330 are retained thereon. After sealing member 322 has been inverted, the end of the wire may be retracted into the containment tube by user actuation to release the sutures. In such embodiments, at least a portion of sutures 330 may be left in the patient with the prosthetic heart valve 300, and such a portion of the sutures may be biodegradable.

As shown in FIGS. 4A-4F, sealing member 322 is inverted before proximal end 302 of stent 306 has fully radially expanded. However, that need not be the case. In an alternative method of deployment, sealing member 322 may be inverted after proximal end 302 of stent 306 has fully radially expanded.

Other than sealing member 322 described above, all of the sealing members and sealing rings described herein have structures that may provide different surface areas and thicknesses of material at different longitudinal and circumferential positions relative to the stent to provide different advantages in sealing voids or gaps between the stent and the native anatomy when the heart valves are deployed into a patient. Such differences in surface areas and thicknesses of material at certain longitudinal and circumferential positions may make some sealing ring configurations preferable for certain native anatomies and other sealing ring configurations preferable for other native anatomies, depending on the anticipated locations of voids or gaps between a deployed prosthetic heart valve and the native anatomy. Such anticipated locations of voids or gaps between a deployed prosthetic heart valve and the native anatomy may be determined by a variety of methods, including imaging of the native anatomy before deployment of a prosthetic heart valve, for example.

FIGS. 5A and 5B illustrate heart valve 300a, which is the same as heart valve 300 of FIGS. 3A-3C, except that heart valve 300a includes a generally toroidal-shaped sealing ring 325 disposed adjacent free edge 323 of sealing member 322a, which may permit prosthetic heart valve 300a to achieve improved sealing against the native annulus and the native leaflets in some patients.

FIG. 5A shows the inverted condition of sealing member 322a, with sealing ring 325 attached to the sealing member at or near free edge 323. Sealing ring 325 may be annularly disposed around the abluminal surface of stent 306 above proximal end 302 of the prosthetic heart valve (e.g., at a position that will lie within the native valve annulus when the prosthetic heart valve is deployed into a patient). Sealing ring 325 may have a radius larger than that of valve assembly 308a, the larger radius of the sealing ring being capable of filling and/or blocking blood flow through gaps between prosthetic heart valve 300a and the native valve annulus.

Sealing ring 325 may be formed of the same material as both sealing member 322a and cuff 312 and may be formed integrally with both of these members from a single piece of material. In such an embodiment, sealing ring 325 may be a rolled end portion of sealing member 322a. Cuff 312, sealing member 322a, and sealing ring 325 may be made of any one or more of the materials described above with respect to sealing ring 322, such as, for example, a thin fabric material, thin porcine pericardial tissue, bovine tissue, tissue with support structures therein, braided or woven fabric, fabric coated with PTFE or collagen, or a multilayered composite of one or more of the aforementioned materials.

Alternatively, sealing ring 325 may be formed of the same material or a different material than sealing member 322a that is sutured, glued or otherwise affixed to sealing member 322a adjacent free edge 323. In such an embodiment, sealing ring 325 may be formed, for example, from a long, thin rectangle of material about 10 mm in width that is folded approximately in half longitudinally, and the opposed longitudinal edges may be stitched to one another to create a flattened tube about 4 mm in diameter. In other examples, such a flattened tube may be between about 2 mm and about 6 mm in diameter. The lateral ends of the flattened tube may be stitched to one another to create sealing ring 325.

As can be seen in FIG. 5B, when sealing member 322a is in the extended condition, sealing ring 325 is disposed on a surface 326 facing radially inward toward the longitudinal axis of stent 306. When sealing member 322a is moved to the inverted condition shown in FIG. 5A, using the method shown in FIGS. 4A-4F for example, surface 326 of the sealing member will face radially outward away from the longitudinal axis of stent 306, and sealing ring 325 will face radially outward as well. When sealing member 322a is in the extended condition (FIG. 5B), its typical condition when positioned within a delivery device, the entirety of sealing ring 325 lies below proximalmost junctions 309a of stent 306, enabling a smaller crimped profile to be achieved compared to when the sealing member is in the inverted condition (FIG. 5A).

Although sealing ring 325 is shown in FIGS. 5A and 5B as having a circular cross-section, that need not be the case. Sealing ring 325 may be flattened in the flow direction, or it may have a cross-section that is square, rectangular, triangular, or other shapes. It is to be understood that all of the "sealing rings" described herein are not to be understood to be limited to having a circular cross-section. Any of the sealing rings described herein may be flattened in the flow direction, or they may have a cross-section that is square, rectangular, triangular, or other shapes.

FIG. 5C illustrates heart valve 300b, which is the same as heart valve 300a of FIGS. 5A and 5B, except that heart valve 300b includes a second sealing ring 327 disposed adjacent sealing ring 325. The presence of second sealing ring 327 along with sealing ring 325 may permit prosthetic heart valve 300b to achieve improved sealing against the native annulus and the native leaflets in some patients.

When sealing member 322a is in the inverted condition shown in FIG. 5C, second sealing ring 327 is disposed proximally of sealing ring 325, between sealing ring 325 and proximalmost junctions 309a of stent 306, facing radially outward away from the longitudinal axis of the stent. When sealing member 322a is in the extended condition (not shown), second sealing ring 327 is disposed distally of sealing ring 325 on surface 326, facing radially inward toward the longitudinal axis of stent 306.

In one example (not shown), second sealing ring 327 may be spaced apart from sealing ring 325 and positioned adjacent proximal end 302 of stent 306 when sealing member 322a is in the inverted condition (e.g., at a position that will lie at least partially below the native valve annulus when the prosthetic heart valve is deployed into a patient). Although FIG. 5C shows sealing member 322a with two sealing rings, the sealing member may include more than two sealing rings arranged sequentially along the sealing member.

Second sealing ring 327 may be formed of the same material as sealing member 322a, and/or cuff 312, and/or sealing ring 325, and may be formed integrally with one or more of these members from a single piece of material. Alternatively, second sealing ring 327 may be formed of the same material or a different material than sealing member 322a, and/or cuff 312, and/or sealing ring 325 that is sutured, glued or otherwise affixed to sealing member 322a adjacent sealing ring 325. In such an embodiment, second sealing ring 327 may be formed, for example, from a long, thin rectangle of material about 10 mm in width that is folded approximately in half longitudinally, and the opposed longitudinal edges may be stitched to one another to create a flattened tube about 4 mm in diameter. The lateral ends of the flattened tube may be stitched to one another to create second sealing ring 327.

When sealing member 322b is in the extended condition (not shown), its typical condition when positioned within a delivery device, the entirety of both sealing ring 325 and sealing ring 327 lies below proximalmost junctions 309a of stent 306, enabling a smaller crimped profile to be achieved compared to when the sealing member is in the inverted condition (FIG. 5C). Although sealing rings 325 and 327 of prosthetic heart valve 300b are shown in FIG. 5C as having an identical structure, that need not be the case. In other embodiments, the two sealing rings may have structures that are different from one another, such as a combination of a flat toroidal sealing ring and a zig-zag sealing ring, such as sealing ring 525e shown in FIG. 5E and described below.

FIGS. 5D-5G illustrate variants of sealing rings that may be used with prosthetic heart valves 300a or 300b in addition to or in place of the sealing rings shown in FIGS. 5A-5C. Each of sealing rings 525d-525g shown in FIGS. 5D-5G may be formed in the same manner, attached to the sealing member in the same manner, and made of the same material or materials described above with reference to sealing rings 325 and 327. Each of the sealing rings 525d-525g may be attached to a sealing member in any location along the longitudinal axis of the sealing member. A prosthetic heart valve, such as prosthetic heart valve 300a, may include one of sealing rings 525d-525g, or alternatively, the prosthetic heart valve may include two or more of the sealing rings, as shown in FIG. 5C.

FIG. 5D shows sealing ring 525d in the shape of a bent or saddle-shaped toroid that alternates between peaks 560d and valleys 570d around the circumference of the sealing ring, the peaks and valleys being substantially evenly distributed about the circumference. As shown in FIG. 5D, sealing ring 525d may have two peaks 560d and two valleys 570d, but may have other numbers of peaks and valleys, such as three, for example, as will be described below with reference to FIGS. 6A and 6B.

FIG. 5E shows sealing ring 525e having a zig-zag shape that alternates between peaks 560e and valleys 570e around the circumference of the sealing ring, the peaks and valleys being substantially evenly distributed about the circumference. As shown in FIG. 5E, sealing ring 525e may have nine peaks 560e and nine valleys 570e, but may have other numbers of peaks and valleys, such as three or six, for example. A sealing ring having a zig-zag shape may be stitched or otherwise attached to a cuff such that the sealing ring will generally follow the contour of the struts when the cuff is moved to an inverted condition such as that shown in FIG. 5A. However, in other embodiments, sealing ring 525e may be attached to the cuff at other locations.

FIG. 5F shows sealing ring 525f having a zig-zag shape with alternating peak heights. Sealing ring 525f alternates between peaks 560f and valleys 570f around the circumference of the sealing ring, the peaks and valleys being substantially evenly distributed about the circumference. As shown in FIG. 5F, sealing ring 525f may have nine peaks 560f and nine valleys 570f, but may have other numbers of peaks and valleys, such as three or six, for example.

Peaks 560f include low peaks 561 that extend by a first height H1 above valleys 570f and high peaks 562 that extend by a second height H2 above the valleys, the second height being greater than the first height. As shown in FIG. 5F, peaks 560f may include four low peaks 561 and four high peaks 562, with one low peak separating adjacent ones of the high peaks. In other embodiments, there may be other numbers of high and low peaks. For example, a sealing ring having varying peak heights may include six low peaks and three high peaks, with two low peaks separating adjacent ones of the high peaks. In another example, a sealing ring having varying peak heights may include three low peaks and six high peaks, with two high peaks separating adjacent ones of the low peaks.

FIG. 5G shows sealing ring 525g having a toroidal shape, similar to the toroidal-shaped sealing ring 325 shown in FIGS. 5A and 5B. Sealing ring 525g has openings 563 in a top surface 564 thereof. Openings 563 may be round holes or may be holes having any other shapes or slits having any shape. Sealing ring 525g may be attached to a cuff of a prosthetic heart valve in a similar manner as that described above with reference to sealing ring 325 shown in FIGS. 5A and 5B.

When sealing ring 525g is attached to a cuff of a prosthetic heart valve, openings 563 and top surface 564 will preferably face toward the distal end of the stent. When deployed in a patient, openings 563 may allow sealing ring 525g to fill with blood, which may augment the ability of the sealing ring to seal against the native aortic annulus or other native tissue structures. Instead of or in addition to openings 563, sealing ring 525g may include expanding materials within the interior of the sealing ring, such as polyacrylimide or other hydroscopic materials, PVA, shape memory foam, bovine gelatin or collagen, or the like. As these materials come in contact with blood, they expand, again augmenting the ability of the sealing ring to seal against the native tissue.

FIG. 5H is a radial cross-section of sealing ring 525h having features that may be incorporated into any of the sealing rings described herein. Sealing ring 525h may be formed in the same manner, attached to the cuff in the same manner, and made of the same material or materials as described above with reference to sealing rings 325 and 327.

Top surface 564 of sealing ring 525h may be made of a porous material having many small openings 563h that are adapted to allow unidirectional blood flow into interior 565 of the sealing ring. Sealing ring 525h may have a bottom surface 566 without openings, and therefore may be substantially less permeable than top surface 564. Bottom surface 566 may be made of a low-porosity material such as a tightly-woven fabric that may have a collagen or PVA coating, for example. Sealing ring 525h may be coated on the exterior of top surface 564 and/or bottom surface 566 with a material (e.g., Ag or a drug compound) to prevent a thrombus or infection from forming thereon. Blood that flows into interior 565 of sealing ring 525h may coagulate and/or in-grow into the material of sealing ring 525h, which may help provide stiffness to the sealing ring in a radial direction.

FIGS. 6A-6F illustrate prosthetic heart valve configurations that have embodiments of sealing rings that are variants of sealing ring 325 shown in FIGS. 5A and 5B, which sealing ring embodiments include stored energy elements in the form of springs that are configured to force portions of the outer edge of the sealing ring away from the cuff in locations at which voids or gaps between the stent and the native anatomy are present.

Each of sealing rings 625a-625f shown in FIGS. 6A-6F may be formed in the same manner, attached to sealing member 622 in the same manner, moved to the inverted condition along with the sealing member in the same manner, and made of the same material or materials described above with reference to sealing ring 325, with the exception of the addition of a stored energy element. Sealing rings 625a and 625c-625f may each be attached to sealing member 622 in any position along the length of the sealing member. A prosthetic heart valve, such as prosthetic heart valve 600, may include one of sealing rings 625a or 625c-625f, or alternatively, two or more of the sealing rings. Each of sealing rings 625a and 625c-625f may be used to replace or to supplement sealing rings 325 and/or 327 in prosthetic heart valve 300a or 300b.

Figure 6A:
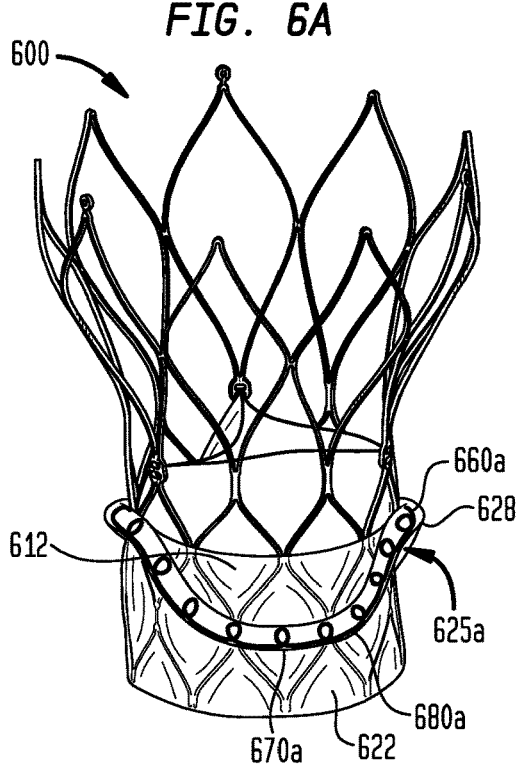
FIG. 6A is a perspective view of another embodiment of a prosthetic heart valve having a sealing ring for filling irregularities between the heart valve and the native valve annulus in accordance with the present disclosure.
Figure 6B:
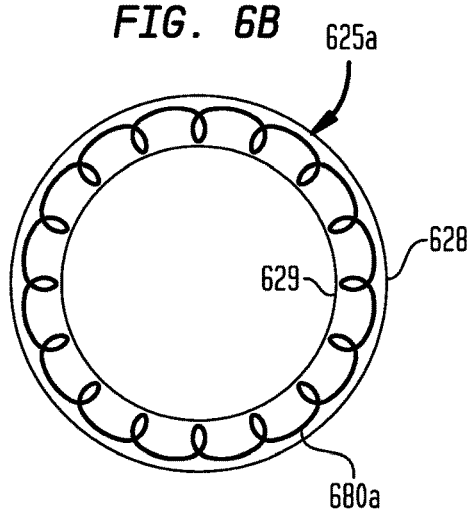
FIG. 6B is a highly schematic top view of the sealing ring of FIG. 6A, without the other heart valve structures.

FIGS. 6A and 6B show sealing ring 625a in the shape of a bent or saddle-shaped toroid similar to sealing ring 525d shown in FIG. 5D, except that sealing ring 625a has three peaks 660a and three valleys 670a substantially evenly distributed about the circumference of the sealing ring. Sealing ring 625a has a stored energy element in the form of coiled spring 680a that extends continuously through the interior of the sealing ring or through substantial portions of the sealing ring.

At least partially due to the capability of spring 680a to store energy, sealing ring 625a (and the other sealing rings disclosed herein that incorporate spring elements) may have a spring bias that provides a force in a radially outward direction when the sealing ring is radially compressed. To provide this spring bias, each spring 680a (and the other spring elements in the sealing rings disclosed herein) may be made from a material having a shape memory, such as nitinol wire or spring steel.

When prosthetic heart valve 600 is radially compressed inside a delivery device, spring 680a will be under radial compression against its bias. When prosthetic valve 600 is initially released from the delivery device with sealing member 622 in the extended condition (not shown), sealing ring 625a will be facing radially inward from the surface of the sealing member, and spring 680a will radially expand according to the bias of the spring. When sealing member 622 is moved to the inverted condition shown in FIG. 6A, sealing ring 625a will be facing radially outward from the surface of the sealing member, and spring 680a will further radially expand so that outer edge 628 of sealing ring 625a will move radially outward from inner edge 629.

Figure 6C:
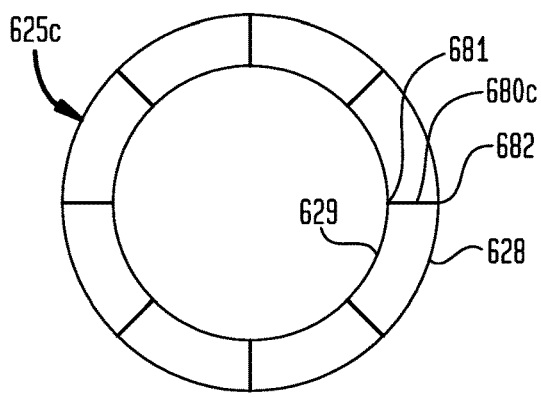
FIGS. 6C-6F are highly schematic top views of alternative sealing ring embodiments that can be used with the stent, cuff, and leaflets of FIG. 6A.

As shown in FIG. 6C, sealing ring 625c has a plurality of stored energy elements in the form of springs 680c circumferentially spaced apart from one another about the interior of the sealing ring. Each spring 680c has a first end 681 located at inner edge 629 of sealing ring 625c and a second end 682 located at outer edge 628. Each spring 680c preferably extends away from inner edge 629 in a direction substantially perpendicular to the flow direction through the stent to which sealing ring 625c is attached. When a sealing member having sealing ring 625c attached thereto is moved to an inverted condition such as that shown in FIG. 6A, second end 682 of each spring 680c preferably moves radially outward from inner edge 629 according to its bias, thereby pushing outer edge 628 of the sealing ring away from the inner edge. The springs 680c may each be flat leaf springs, or they may be portions of coil springs in the form of a spiral or a circular hoop. In embodiments where the springs 680c are in the form of a spiral or circular hoop, first end 681 and second end 682 of each spring are understood to be the portions of the spiral or circular hoop closest to inner edge 629 and outer edge 628, respectively.

Figure 6D:
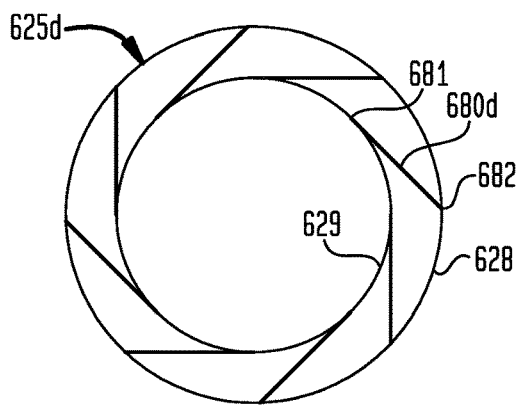

FIG. 6D shows sealing ring 625d that is the same as sealing ring 625c of FIG. 6C, except that each spring 680d is oriented at an acute angle with respect to the circumference of the stent. When viewed from a top surface of sealing ring 625d, as shown in FIG. 6D, springs 680d may be oriented in a clockwise direction about the longitudinal axis of the sealing ring from their first ends 681 to their second ends 682. Alternatively, springs 680d may be oriented in a counterclockwise direction about the longitudinal axis of the sealing ring from their first ends 681 to their second ends 682. The springs 680d may each be flat leaf springs, or they may be portions of coil springs in the form of a spiral or a circular hoop. In embodiments where the springs 680*d* are in the form of a spiral or circular hoop, first end 681 and second end 682 of each spring are understood to be the portions of the spiral or circular hoop closest to inner edge 629 and outer edge 628, respectively.

Figure 6E:
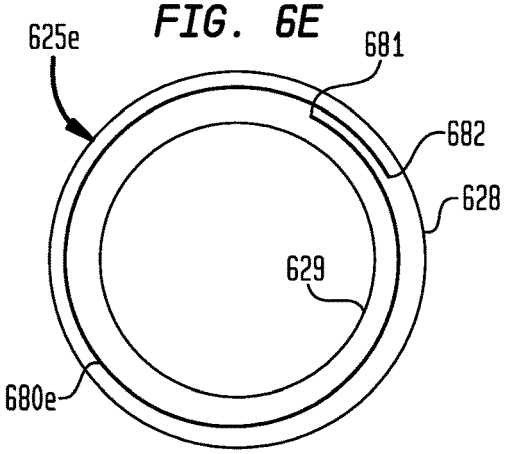

FIG. 6E shows sealing ring 625*e* that is the same as sealing ring 625*a* of FIGS. 6A and 6B, except that the stored energy element is in the form of leaf spring 680*e* that extends in at least one complete loop through the sealing ring, such that first end 681 and second end 682 of the spring overlap one another in the circumferential direction of the sealing ring. Similar to sealing ring 625*a*, when a prosthetic valve having sealing ring 625*e* is released from a delivery device and the sealing member is moved to the inverted condition shown in FIG. 6A, spring 680*e* will radially expand, such that outer edge 628 of the sealing ring moves radially outward from inner edge 629 according to the bias of the spring.

Figure 6F:
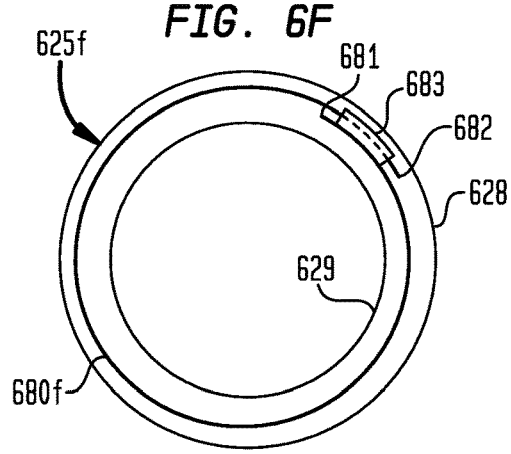

FIG. 6F shows sealing ring 625*f* that is the same as sealing ring 625*e* of FIG. 6E, except that leaf spring 680*f* includes ratchet element 683 that slidably couples either first end 681 or second end 682 of the spring to another portion of the spring. Ratchet element 683 includes first and second portions that move past one another to allow the leaf spring to radially expand, but that engage with one another to prevent the leaf spring from radially contracting. Similar to sealing ring 625*e*, when a prosthetic valve having sealing ring 625*f* is released from a delivery device and the sealing member is moved to the inverted condition shown in FIG. 6A, spring 680*f* will radially expand, such that outer edge 628 of the sealing ring moves radially outward from inner edge 629 according to the bias of the spring. Once spring 680*f* has expanded, it will substantially maintain its diameter due to the engagement of the first and second portions of ratchet element 683, preventing the spring from re-collapsing to a smaller radial profile.

Figure 7A:
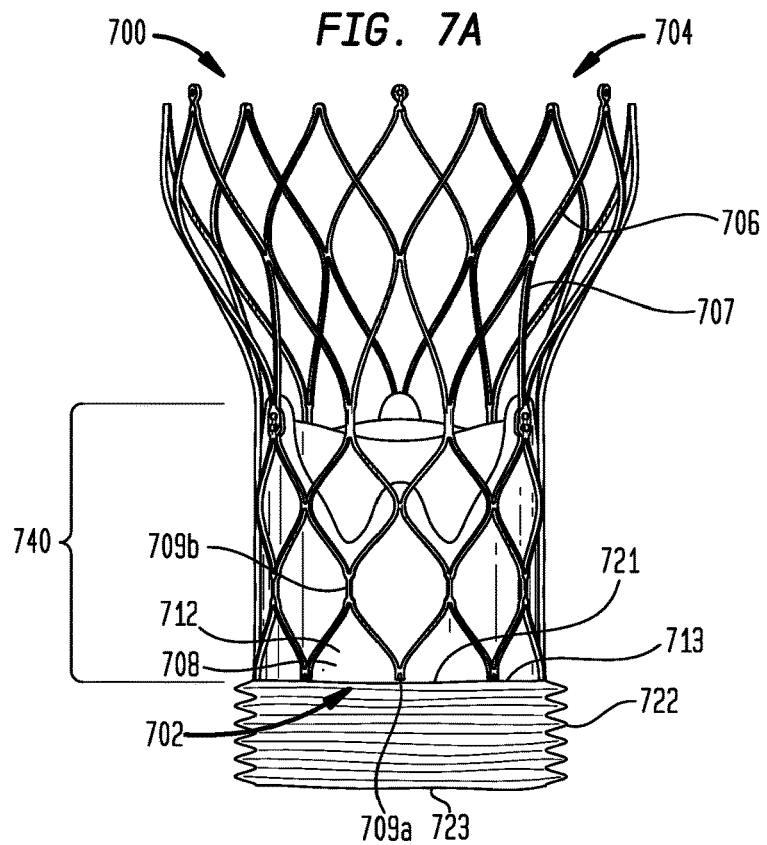
FIG. 7A is a highly schematic side view of an embodiment of a prosthetic heart valve having a sealing member for filling irregularities between the heart valve and the native valve annulus in accordance with the present disclosure, with the sealing member in a contracted condition.
Figure 7B:
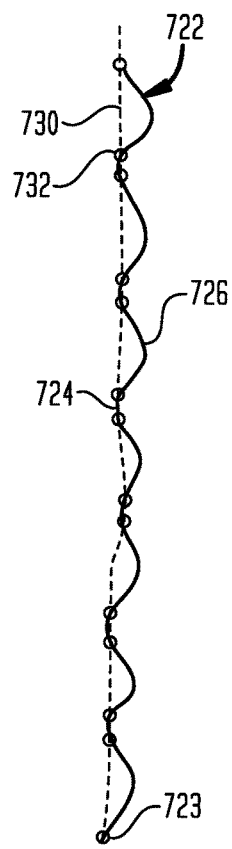
FIG. 7B is a highly schematic partial cross-sectional view of the sealing member of FIG. 7A, with the sealing member in an extended condition.
Figure 7C:
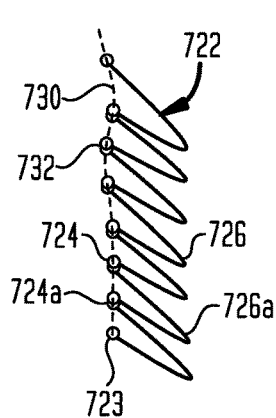
FIG. 7C is a highly schematic partial cross-sectional view of the sealing member of FIG. 7A, with the sealing member in the contracted condition.

FIGS. 7A-7C illustrate prosthetic heart valve 700, which is the same as prosthetic heart valve 300 of FIGS. 3A-3C, except that prosthetic heart valve 700 includes sealing member 722 that, rather than inverting, is configured to move from an extended condition shown in FIG. 7B to a compressed or bunched condition shown in FIGS. 7A and 7C which may permit prosthetic heart valve 700 to achieve improved sealing against the native annulus and the native leaflets in some patients. In the compressed condition, sealing member 722 may have a bunched shape somewhat resembling the bunched shape of a roman shade, in which peaks 726 droop to a position proximal of adjacent valleys 724.

As can be seen in FIG. 7A, prosthetic heart valve 700 extends between proximal end 702 and distal end 704, and may generally include stent 706 formed of a plurality of struts 707, and valve assembly 708 having a plurality of leaflets and cuff 712.

Valve assembly 708 includes a generally smooth sealing member 722 that extends from a proximal end 713 of cuff 712. Proximal end 721 of sealing member 722 at which the cuff 712 and sealing member meet may be disposed at proximalmost junctions 709*a* of stent 706. In one example (not shown), proximal end 721 of sealing member 722 may be attached to cuff 712 and/or stent 706 between proximalmost junctions 709*a* of stent 706 and upper junctions 709*b* of the proximalmost struts of the stent. In other examples (not shown), proximal end 721 of sealing member 722 may be attached to cuff 712 and/or stent 706 anywhere along annulus section 740 of the stent, so that in the compressed condition, the sealing member may cover a portion of or all of the annulus section of the stent.

Sealing member 722 may include valley portions 724 and peak portions 726 that alternate in the longitudinal direction of stent 706. A plurality of sutures 730 may extend through apertures 732 located within the valley portions. Sealing member 722 may include at least two sutures 730, or a multitude of sutures spaced around the circumference thereof. Sutures 730 may extend from a location adjacent free edge 723 of sealing member 722 to the proximal end of a delivery device through a containment tube (not shown) extending within a distal sheath of the delivery device. When sealing member 722 is in the extended condition, shown in FIG. 7B, valley portions 724 and peak portions 726 may be generally flattened, such that the peak portions extend radially outward only a small distance relative to the valley portions.

In some embodiments, when sealing member 722 is in the extended condition, the valley portions 724 and peak portions 726 may be substantially completely flattened, so that the sealing member has a shape similar to the shape of sealing member 322 shown in FIG. 3A.

Removable sutures 730 may be pulled by a user to move sealing member 722 from the extended condition (FIG. 7B) to the compressed condition (FIGS. 7A and 7C). As the sutures are pulled by the user, free edge 723 of sealing member 722 is moved toward proximal end 702 of stent 706. As free edge 723 moves distally, the material of sealing member 722 buckles at the locations of valley portions 724 and peak portions 726, until the valley portions are pulled to a position adjacent one another with the peak portions extending radially outward therefrom. In the compressed condition of sealing member 722 shown in FIG. 7C, each peak 726 may droop below the adjacent proximal valley 724. In other words, each peak 726 may have a central portion 726*a* that extends proximally of the respective proximally adjacent valley 724*a*.

In the extended condition of sealing member 722 shown in FIG. 7B, free edge 723 may be located a first distance proximally of proximal end 702 of stent 706, and in the compressed condition of the sealing member shown in FIGS. 7A and 7C, the free edge may be located a second distance proximally of the proximal end of the stent, the first distance being greater than the second distance. Preferably, the first distance may be at least double the second distance. In other examples, the first distance may be at least triple the second distance, or the first distance may be at least quadruple the second distance.

Once sealing member 722 has been moved to the compressed condition, a user may cut sutures 730 at the proximal end of the delivery device, and may pull one end of each suture until the suture withdraws from apertures 732 in sealing member 722 and from the delivery device.

Similar to the alternative methods of deploying prosthetic heart valve 300*a* having sealing member 322*a* shown in FIGS. 4A-4F, sealing member 722 may be moved to the compressed condition either before proximal end 702 of stent 706 has fully radially expanded, or after the proximal end of the stent has fully radially expanded.

Figure 7D:
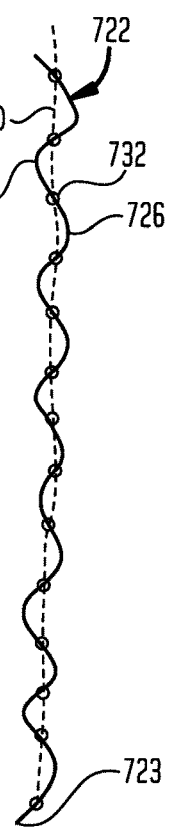
FIG. 7D is a highly schematic partial cross-sectional view of a variation of the sealing member of FIG. 7A, with the sealing member in an extended condition.
Figure 7E:
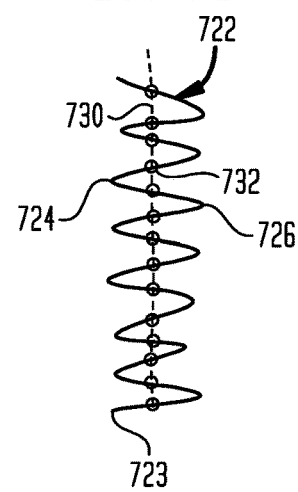
FIG. 7E is a highly schematic partial cross-sectional view of a variation of the sealing member of FIG. 7A, with the sealing member in a contracted condition.

FIGS. 7D and 7E illustrate sealing member 722*a* that is a variant of sealing member 722. In sealing member 722*a*, apertures 732 through which removable sutures 730 extend are located between valleys 724 and peaks 726 of the sealing member. As a result, when sealing member 722*a* is moved from the extended condition (FIG. 7D) to the compressed condition (FIG. 7E), the material of the sealing member buckles so that valleys 724 are located radially inward from apertures 732, and peaks 726 are located radially outward from the apertures. In the compressed condition shown in FIG. 7E, sealing member 722a may have a bunched shape somewhat resembling the bunched shape of a cellular shade, in which peaks 726 and valleys 724 may have a regular zig-zag pattern.

In the extended condition of sealing member 722a shown in FIG. 7D, free edge 723 may be located a first distance proximally of proximal end 702 of stent 706, and in the compressed condition of the sealing member shown in FIG. 7E, the free edge may be located a second distance proximally of the proximal end of the stent, the first distance being greater than the second distance. Preferably, the first distance may be at least double the second distance. In other examples, the first distance may be at least triple the second distance, or the first distance may be at least quadruple the second distance.

In a variant (not shown) of sealing members 722 and 722a shown in FIGS. 7A-7E, the sealing members may be made of a material, such as a nitinol sheet, that is configured to move to the compressed condition shown in FIGS. 7A, 7C, or 7E when the material comes in contact with heat (e.g., the heat from a patient's bloodstream). In such a variant, sutures 730 may be omitted, because the sealing members can move from the extended condition to the compressed condition merely by retracting the distal sheath of the delivery device, without the need to pull on sutures.

In another variant (not shown) of sealing members 722 and 722a shown in FIGS. 7A-7E, the sealing members may include one or more of any of the sealing rings shown and described above with reference to FIGS. 5A through 6F. Such sealing rings may extend circumferentially around an outwardly-facing surface of the sealing members 722 or 722a.

Although the sutures 730 of FIGS. 7A-7E are described herein as extending through apertures in sealing member 722 and sealing member 722a, the apertures need not be formed in the sealing member before the sutures are attached to the sealing member. The invention contemplates threading the sutures 730 directly through the material of sealing member 722. For example, in an embodiment where sealing member 722 is made of a fabric, sutures 730 may be threaded through gaps extending between fibers of the fabric, such that no additional apertures are created by the action of threading the sutures through the sealing member.

In a variation, sutures 730 of FIGS. 7A-7E may be replaced with other filamentary elements, such as at least one polymer wire, braided metal wire, Nitinol wire, cord, ribbon, or any other connecting member that may be used to pull sealing member 722 to a compressed condition (e.g., FIG. 7A, 7C, 7E.)

In another variant (e.g., FIG. 8C), sutures 730 of FIGS. 7A-7E may be replaced with elastomeric elements that may automatically (i.e., without actuation by the user independent from actuation of the distal sheath) move sealing member 722 from the extended condition to the compressed condition during unsheathing of the valve. A description of this variation is set forth in detail below, with respect to FIG. 8C.

FIGS. 8A and 8B illustrate prosthetic heart valve 800, which is the same as prosthetic heart valve 300 of FIGS. 3A-3C, except that rather than having removable sutures 330, prosthetic heart valve 800 includes retractable filaments 830 that are configured to shorten without being pulled by a user. Filaments 830 may extend along the outside surface of sealing member 822 and cuff 812 at spaced positions around the circumference of the sealing member from a proximal position 832 at which the filaments are attached at or adjacent free edge 823 of the sealing member to a position on stent 806. Although filaments 830 are shown in FIGS. 8A and 8B extending from proximal position 832 to distal position 834 at or near distal end 804 of stent 806, that need not be the case. Distal position 834 at which filaments 830 are attached to stent 806 may be any location along the stent that will be located distally of free edge 823 of sealing member 822 when the sealing member moves to the inverted condition shown in FIG. 8B.

Filaments 830 may have an unstressed length and a shape memory such that, when a longitudinal force is applied to stretch the filaments to an extended length, the filaments have a spring bias that tends to shorten the filaments back to their unstressed length. Filaments 830 may be made from elastic sutures, for example, and preferably are made of a biocompatible material so that they may be left in a patient after the deployment of prosthetic heart valve 800.

When prosthetic heart valve 800 is radially compressed within distal sheath 842 of delivery device 840, sealing member 822 is radially compressed and held in the extended condition shown in FIG. 8A by a frictional force acting between the distal sheath and the sealing member. In this extended condition, filaments 830 are stretched to their extended length so as to be under tension.

To move sealing member 822 from the extended condition to the inverted condition shown in FIG. 8B, the user may retract distal sheath 842 off of proximal end 802 of stent 806, thereby removing the frictional force keeping the sealing member in the extended condition and filaments 830 at their extended length. Once distal sheath 842 is retracted, the tension in filaments 830 will cause them to shorten, thereby pulling free edge 823 of sealing member 822 in a distal direction and moving the sealing member to the inverted condition shown in FIG. 8B.

In an alternative embodiment, filaments 830 may be made from shrinkable nitinol, a shrinkable material that has a first extended length, and when the filaments are exposed to blood, the filaments shrink to a second contracted length less than the first extended length. In such an embodiment, the filaments 830 will not be under tension. Instead, when distal sheath 842 is retracted, filaments 830 will contact blood, and the resulting rise in the temperature of the filaments will cause them to shorten, thereby pulling free edge 832 of sealing member 822 in a distal direction and moving the sealing member to the inverted condition shown in FIG. 8B.

FIG. 8C illustrates prosthetic heart valve 800a, which is the same as prosthetic heart valve 800, except that sealing member 822a is configured to shorten to the compressed condition shown in FIGS. 7A-7E, rather than invert. When prosthetic heart valve 800a is in an extended condition, it may look similar to the extended condition of prosthetic heart valve 800 shown in FIG. 8A. However, once the distal sheath of the delivery device is retracted off of proximal end 802 of stent 806, filaments 830 will shorten as described above, thereby pulling free edge 823 of sealing member 822a in a distal direction and moving the sealing member to the compressed condition shown in FIG. 8C.

Although filaments 830 are shown in FIG. 8C extending from proximal position 832 to distal position 834 at or near distal end 804 of stent 806, that need not be the case. Distal position 834 at which filaments 830 are attached to stent 806 may be any location along the stent that will be distal of free edge 823 of sealing member 822a when the sealing member moves to the compressed condition shown in FIG. 8C.

In an alternative embodiment (not shown), filaments 830 may be replaced with an elastomeric strip (and/or another energy storage element) stitched into or otherwise attached to sealing member 822a in a tensioned state. In such an embodiment, the elastomeric strips will be under tension when sealing member 822a is in the extended condition. When sealing member 822a of prosthetic heart valve 800a is unsheathed, the elastomeric strips may automatically contract, thereby moving sealing member 822a to the compressed condition.

FIGS. 9A and 9B illustrate prosthetic heart valve 900, which is the same as prosthetic heart valve 800, except that sealing member 922 is biased to move to a rolled condition to form sealing ring 925 as shown in FIG. 9B, rather than to an inverted condition.

As can be seen in FIG. 9A, stent 906 may include a plurality of independent fingers 911 at spaced positions around the circumference of sealing member 922, each finger extending proximally along sealing member 922 to a free end 913 at least 8 mm from one of proximalmost junctions 909a of the stent. In other examples, each finger may extend proximally along sealing member 922 to a free end 913 at least 12 mm from the proximalmost junction, or each finger may extend proximally along the sealing member to the free end at least 16 mm from the proximalmost junction. Free ends 913 of fingers 911 may be attached to sealing member 922 adjacent free edge 923 thereof. Fingers 911 may have a shape memory that tends to roll the fingers into the spiral shape shown in FIG. 9B when the fingers are not being forced into a substantially straight configuration.

When prosthetic heart valve 900 is radially compressed within the distal sheath of a delivery device, sealing member 922 is radially compressed and held in the extended condition shown in FIG. 9A by a frictional force acting between the distal sheath and the sealing member. In this extended condition, fingers 911 are straightened against their bias.

To move sealing member 922 from the extended condition to the rolled condition shown in FIG. 9B, the user may retract the distal sheath off of the proximal end 902 of stent 906, thereby removing the force that is keeping the sealing member in the extended condition and fingers 911 in their straight configuration. Once the distal sheath is retracted, fingers 911 will assume the rolled condition, thereby rolling sealing member 922 outwardly in the direction of the distal end of stent 906 to form sealing ring 925 such that a distal surface 923 of the sealing ring is at substantially the same height as the proximalmost junctions 909a of the stent.

As shown in FIG. 9B, sealing member 922 may be rolled into a generally toroidal-shaped sealing ring 925 near proximal end 902 of stent 906 (e.g., at a position that will lie at least partially below the native valve annulus when the prosthetic heart valve is deployed into a patient). Sealing ring 925 may be formed of one complete revolution of sealing member 922, or of a series of revolutions (e.g., two, three or more revolutions of the sealing member).

Figure 10A:
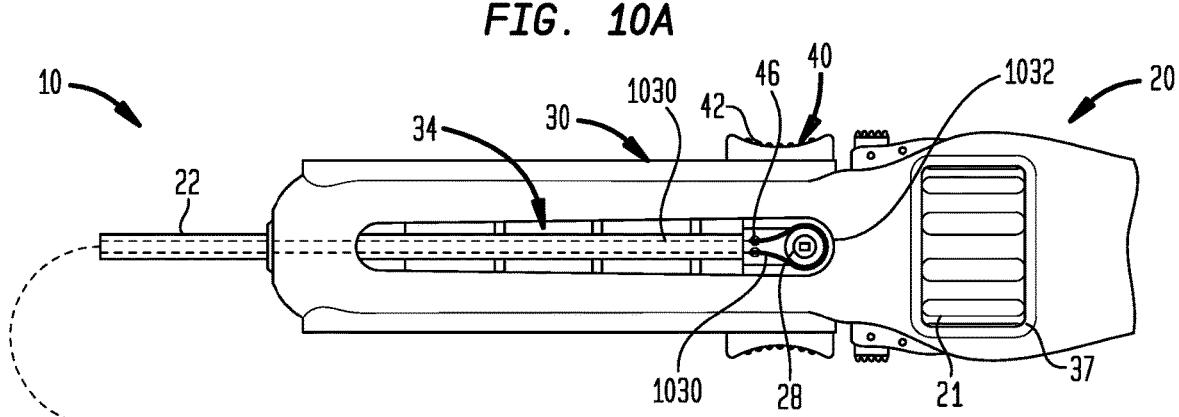
FIG. 10A is a top plan view of a portion of an operating handle for a transfemoral delivery device for a collapsible prosthetic heart valve, shown with a partial longitudinal cross-section of the distal portion of a transfemoral catheter assembly.
Figure 10B:
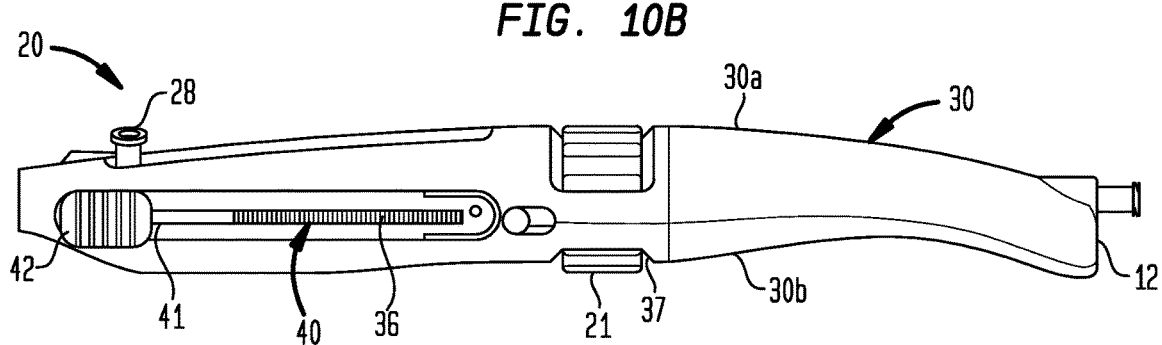
FIG. 10B is a side view of the handle of FIG. 1A.

Referring now to FIGS. 10A and 10B, an exemplary transfemoral delivery device 10 for collapsible prosthetic heart valves of the types described above (or other types of implantable medical devices) has catheter assembly 16 for delivering the heart valve to and deploying the heart valve at a target location, and operating handle 20 for controlling deployment of the valve from the catheter assembly. Delivery device 10 extends from proximal end 12 (FIG. 10B) to atraumatic tip 14 at the distal end of catheter assembly 16. Catheter assembly 16 is adapted to receive a collapsible prosthetic heart valve (e.g., prosthetic heart valve 300 shown in FIGS. 3A-3C) in compartment 23 defined around inner shaft 26 and covered by distal sheath 24.

Inner shaft 26 may extend through operating handle 20 and catheter assembly 16 to atraumatic tip 14 of the delivery device, and includes retainer 25 affixed thereto at a spaced distance from atraumatic tip 14 and adapted to hold a collapsible prosthetic valve in compartment 23. Retainer 25 may have recesses 80 therein that are adapted to hold corresponding retention members of the valve. Inner shaft 26 may be made of a flexible material such as braided polyimide or polyetheretherketone (PEEK), for example. Using a material such as PEEK may improve the resistance of inner shaft 26 to kinking while catheter assembly 16 is tracking through the vasculature of a patient.

Distal sheath 24 surrounds inner shaft 26 and is slidable relative to the inner shaft such that it can selectively cover or uncover compartment 23. Distal sheath 24 is affixed at its proximal end to outer shaft 22, the proximal end of which is connected to operating handle 20 in a manner to be described below. Distal end 27 of distal sheath 24 abuts a proximally-facing abutment surface 15 of atraumatic tip 14 when the distal sheath is fully covering compartment 23, and is spaced apart from the proximally-facing abutment surface 15 when the compartment is at least partially uncovered.

Operating handle 20 is adapted to control deployment of a prosthetic valve located in compartment 23 by permitting a user to selectively slide outer shaft 22 proximally or distally relative to inner shaft 26, thereby respectively uncovering or covering the compartment with distal sheath 24. In some examples, operating handle 20 is configured to repeatedly cover or uncover the compartment with distal sheath 24. For example, compartment 23 may be uncovered to expose a valve and allow it to expand at a target location. Once at the location, the functionality and positioning of the valve may be examined prior to complete release of the valve. If the functioning or position of the valve is improper, distal sheath 24 may be advanced to cover the compartment and the valve may be redeployed in a different position or orientation.

Outer shaft 22 may be made of a flexible material such as nylon 11 or nylon 12, and may have a round braid construction (i.e., round cross-section fibers braided together) or a flat braid construction (i.e., rectangular cross-section fibers braided together), for example. The proximal end of inner shaft 26 may be connected in a substantially fixed relationship to outer housing 30 of operating handle 20, and the proximal end of outer shaft 22 may be affixed to carriage assembly 40 that is slidable along a longitudinal axis of the handle housing, such that a user can selectively slide the outer shaft relative to the inner shaft by sliding the carriage assembly relative to the housing. A hemostasis valve 28 may be provided and may include an internal gasket adapted to create a seal between inner shaft 26 and the proximal end of outer shaft 22.

Handle housing 30 includes a top portion 30a and a bottom portion 30b. The top and bottom portions 30a and 30b may be individual pieces joined to one another as shown in FIG. 10B. Collectively, top and bottom portions 30a and 30b define elongated space 34 in housing 30 in which carriage assembly 40 may travel. Elongated space 34 preferably permits carriage assembly 40 to travel a distance that is at least as long as the anticipated length of the prosthetic valve to be delivered (e.g., at least about 20 mm, 45 mm, or 50 mm), such that distal sheath 24 can be fully retracted from around the prosthetic valve. Carriage assembly 40 has a body portion 41 with threaded rod 36 extending proximally therefrom along the longitudinal axis of housing 30. Carriage assembly 40 may further include a pair of carriage grips 42 each attached to body portion 41 by a respective carriage grip shaft (not shown).

Handle housing 30 further defines a pocket 37 that extends through top portion 30a and bottom portion 30b for receiving deployment actuator 21. Deployment actuator 21 is internally threaded for selective engagement with threaded rod 36. When deployment actuator 21 is in threaded engagement with threaded rod 36, rotation of the deployment actuator in one direction (either clockwise or counterclockwise depending on the orientation of the threads on the threaded rod) causes the threaded rod to move proximally, at the same time pulling body portion 41 of carriage assembly 40 proximally through elongated space 34, and pulling outer shaft 22 and distal sheath 24 proximally relative to inner shaft 26. Similarly, when deployment actuator 21 is in threaded engagement with threaded rod 36, rotation of the deployment actuator in the opposite direction causes the threaded rod to move distally through elongated space 34, which pushes outer shaft 22 and distal sheath 24 distally relative to inner shaft 26. When deployment actuator 21 is disengaged from threaded rod 36, the threaded rod may be translated without rotation of the deployment actuator by a user grasping and moving carriage grips 42.

Handle 20 may also include a resheathing lock adapted to limit the longitudinal movement of carriage assembly 40 proximally within handle housing 30, thereby preventing the user from completing the deployment of a prosthetic valve unintentionally. The initial distance that carriage assembly 40 can travel before being limited by the resheathing lock may be about 80% to about 90% of the length of an exemplary 50 mm valve. Further details of the coupling assembly and embodiments of resheathing locks suitable for use with delivery device 10 are shown and described in co-pending and co-owned U.S. Patent Application Publication No. 2013/0297011, the disclosure of which is hereby incorporated by reference herein.

Figure 10C:
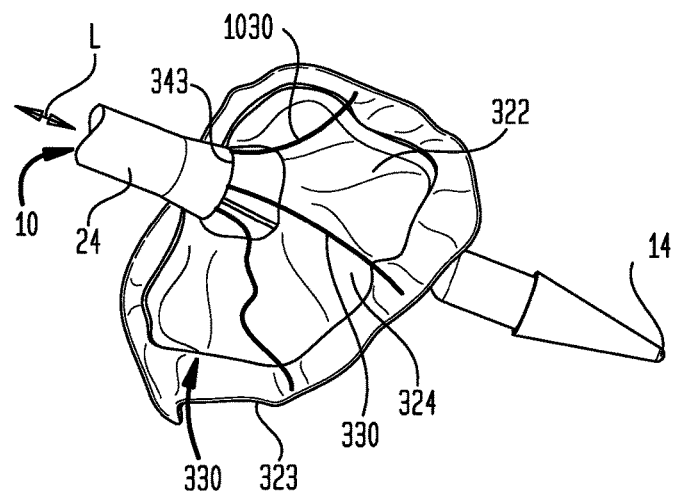
FIG. 10C is a perspective view of an embodiment of a prosthetic heart valve suitable for use with the operating handle of FIG. 10A.

FIG. 10C shows prosthetic valve 300 of FIGS. 3A-3C coupled to delivery device 10 and having sealing member 322 in a partially inverted position. Delivery device 10 may include one or more removable sutures 1030 configured to automatically invert sealing member 322 of prosthetic heart valve 300. Removable sutures 1030 may extend within a lumen of outer shaft 22 from compartment 23 to apertures 46 in carriage assembly 40 at which the proximal ends of the sutures may be connected. Sutures 1030 may take any of the forms and be made of any of the materials described above with respect to sutures 330. Removable sutures 1030 may be connected at their distal ends to respective apertures in sealing member 322 adjacent its free edge 323, and the free ends of each suture may extend proximally to operating handle 20 through outer shaft 22 of delivery device 10.

Sutures 1030 may have proximal end portions 1032 that are connected to apertures 46 in carriage assembly 40, thereby fixing the end portions of the sutures to the carriage assembly for movement therewith. End portions 1032 may be accessible for a user holding operating handle 20 to cut after inversion of sealing member 322.

As shown in FIG. 10A, proximal end portions 1032 of sutures 1030 may be take the form of a single looped suture portion that extends around hemostasis valve 28. In one example, proximal end portions 1032 of sutures 1030 may each terminate in a knot that is wider than the apertures 46, such that the apertures may retain the proximal end portions in a fixed relationship to carriage assembly 40. In another example, proximal end portions 1032 of sutures 1030 may be a single suture portion that extends between apertures 46 without extending around hemostasis valve 28. In other examples, end portions 1032 of sutures 1030 may take any other form that permits a user access to the sutures for cutting and/or removal of the sutures from the delivery device 10, and fixes the sutures to the carriage assembly 40, so that the sutures may be pulled together with the carriage assembly.

To use operating handle 20 to deploy a prosthetic valve that has been loaded into the compartment 23 and covered by distal sheath 24, the user may rotate deployment actuator 21, causing carriage assembly 40 to slide proximally within elongated space 34 in housing 30. Because distal sheath 24 is affixed to outer shaft 22, which in turn is affixed to the carriage assembly 40, and because inner shaft 26 is fixed to housing 30, sliding the carriage assembly proximally relative to the housing will retract the distal sheath proximally from compartment 23, thereby exposing and initiating deployment of the valve located therein.

Because end portions 1032 of sutures 1030 are affixed to carriage assembly 40 for movement therewith, as distal sheath 24, outer shaft 22, and the carriage assembly are moved proximally, the sutures pull free edge 323 of sealing member 322 in the longitudinal direction L toward proximal end 12 of delivery device 10. This pulling of sutures 1030 causes sealing member 322 to automatically (i.e., without the user pulling the sutures independently of moving the carriage assembly) begin to move from the extended condition (FIG. 3A) to the inverted condition (FIG. 3B).

When the deployment procedure has reached a partial deployment of the valve, for example, deployment of about 80% of the length of the valve, the user can evaluate the position of the valve relative to the patient's aortic annulus and may be able to determine whether the valve is functioning properly. If repositioning or removal is desired, the user may resheath the valve, for example, by rotating deployment actuator 21 in the direction opposite that used for deployment. Such rotation will cause threaded rod 36 to progress distally through deployment actuator 21 until carriage assembly 40 has reached the starting position shown in FIG. 10B, thereby re-collapsing the expanded part of the valve as distal sheath 24 is moved distally over compartment 23 and the partially deployed valve. With the valve resheathed, the user can reposition delivery device 10 and commence the deployment procedure once again or simply remove the valve from the patient.

Once the proper positioning of the valve relative to the aortic annulus has been assured, the user may complete the deployment process. The user can slide carriage assembly 40 proximally to complete the deployment of the valve by again rotating deployment actuator 21 in the first direction, thereby releasing the valve from catheter assembly 16. With distal sheath 24 completely withdrawn from the compartment, and carriage assembly 40 at its proximalmost position (FIG. 10A), sealing member 322 will be in the inverted condition. After sealing member 322 has been inverted, a user may cut end portions 1032 of sutures 1030 that extend through apertures 46 of carriage assembly 40. The user may then pull one end of each suture 1030 proximally until the suture withdraws from sealing member 322 and from apertures 46 of carriage assembly 40.

Although the automatic sealing member inversion has been described above with respect to inverting the sealing member of prosthetic heart valve 300 of FIG. 3A, that arrangement may be used to invert the sealing members of any of the other prosthetic heart valves described herein.

FIG. 11 illustrates heart valve 1100, which is the same as heart valve 800 of FIGS. 8A and 8B, except that sealing member of 1122 of heart valve 1100 includes removable pegs 1128 that hold the sealing member in its initial extended condition until a user decides to move the sealing member to an inverted or contracted condition.

Prosthetic heart valve 1100 has energy storage elements 1130 that may be the filaments 830 described above. Energy storage elements 1130 may have an unstressed length and a shape memory such that, when a longitudinal force is applied to stretch the energy storage elements to an extended length, the energy storage elements have a spring bias that tends to shorten the energy storage elements back to their unstressed length. Energy storage elements 1130 may be made from elastic sutures or an elastomeric member, for example, and preferably are made of a biocompatible material so that they may be left in a patient after the deployment of prosthetic heart valve 1100.

Removable pegs 1128 are configured to hold sealing member 1122 is its initial extended condition, such as the extended condition shown in FIG. 11. Pegs 1128 may be rigid reinforcements removably attached to sealing member 1122 that prevent the sealing member from folding to an inverted condition (e.g., FIG. 8B) or a contracted condition (e.g., FIG. 8C) until the pegs are detached from the sealing member by a user. Pegs 1128 are affixed to filaments 1129 (e.g., wires, sutures, or any of the other filamentary structures described above) that may extend from the pegs proximally to a delivery device handle, where they may be accessible for a user to pull.

Pegs 1128 may be removably coupled to sealing member 1122, for example, by filaments such as sutures (not shown) that are configured to break when a threshold amount of force is applied thereto. One filament may couple a peg 1128 to sealing member 1122 adjacent free edge 1123, and another filament may couple the peg to the sealing member adjacent proximal end 1113 of cuff 1112. Alternatively, pegs 1128 may be removably coupled to sealing member 1122 by having each end of the peg engaged in a corresponding pocket (not shown) of the sealing member, for example, having one pocket adjacent free edge 1123 and another pocket adjacent proximal end 1113 of cuff 1112. As shown in FIG. 11, filaments 1129 are affixed to the distal ends of pegs 1128, however, in other embodiments, the filaments may be attached to other portions of the pegs.

When a user decides to move sealing member 1122 to an inverted condition (e.g., FIG. 8B) or a contracted condition (e.g., FIG. 8C), the user may grasp and pull the proximal ends of filaments 1129 in a proximal direction. The proximal force exerted on the pegs 1128 will detach the pegs from sealing member 1122, thereby permitting energy storage elements 1130 to move the sealing member to the inverted or contracted position, in a manner similar to that described above with reference to FIGS. 8B or 8C. Once pegs 1128 have been detached from sealing member 1122, the user may advance the distal sheath of the delivery device (e.g., similar to the delivery device 10 shown in FIGS. 10A and 10B), at which point the pegs and the ends of filaments 1129 attached to the pegs are captured in the valve compartment, so that the pegs will not damage native tissue of the patient during withdrawal of the delivery device from the patient.

Pegs 1128 are preferably removed from sealing member 1122 before aortic end 1132 of prosthetic heart valve 1100 is fully radially expanded in order to eliminate the need to force the pegs between the aortic end of the valve and native tissue of the ascending aorta, potentially resulting in damage to the native tissue.

Although prosthetic heart valve 1100 is described as a variation of prosthetic heart valve 800 of FIGS. 8A and 8B, prosthetic heart valve 1100 may alternatively be a variation of prosthetic heart valve 900 of FIGS. 9A and 9B. In such a variation, the function of energy storage elements 1130 may be replaced by the energy storage function of independent fingers 911, which have a shape memory that tends to roll the fingers into the spiral shape shown in FIG. 9B when the fingers are not being held in a substantially straight configuration. In this variation, when pegs 1128 are detached from sealing member 1122, independent fingers 911 will be free to assume a rolled condition according to their bias, rolling the sealing member to form a sealing ring (as shown in FIG. 9B).

FIGS. 12A-12C illustrate prosthetic heart valve 1200, which is a variation of prosthetic heart valve 1100 of FIG. 11 including a sealing member having an alternate version of the removable pegs. Prosthetic heart valve 1200 includes sealing member 1222 that has removable pegs 1228 that are configured to hold the sealing member in its initial extended condition (FIG. 12A) until a user decides to move the sealing member to a contracted condition (FIGS. 12B and 12C). Similar to pegs 1128, pegs 1228 may be rigid reinforcements removably attached to sealing member 1222 that prevent the sealing member from folding to an inverted condition (e.g., FIG. 8B) or a contracted condition (e.g., FIG. 8C) until the pegs are detached from the sealing member by a user.

Prosthetic heart valve 1200 has energy storage elements that may be the same as those described above with respect to FIG. 11, although those energy storage elements are not shown in FIGS. 12A-12C. The energy storage elements are configured to move sealing member 1222 from its initial extended condition to its contracted condition.

Pegs 1228 are configured to hold sealing member 1222 is its initial extended condition, such as the extended condition shown in FIG. 12A. Similar to pegs 1128, pegs 1228 may be removably coupled to sealing member 1222, for example, by filaments such as sutures that are configured to break when a threshold amount of force is applied thereto, or by having each end of the peg engaged in a corresponding pocket of the sealing member.

Pegs 1228 are affixed to springs 1229 that may extend from the pegs proximally to their fixation to distal sheath 24 of a delivery device, such as delivery device 10 of FIGS. 10A and 10B. Proximal end 1221 of each spring 1229 is affixed to distal sheath 24, so that when the distal sheath is moved proximally by the user to deploy the prosthetic heart valve 1200 within a patient, the springs are stretched in the direction of the longitudinal axis of the distal sheath.

When the pulling force acting on pegs 1228 reaches a predetermined threshold amount, springs 1229 automatically (i.e., without the user pulling the springs independently of moving the distal sheath 24) detach the pegs from sealing member 1222, thereby permitting the energy storage elements to move the sealing member from the extended condition to the contracted condition, in a manner similar to that described above with reference to FIG. 8C. After pegs 1228 have been detached from sealing member 1222, springs 1229 automatically pull the pegs into distal sheath 24, as shown in FIG. 12C. Once pegs 1228 have been pulled into distal sheath 24 and the distal sheath has been moved to cover the valve compartment, the pegs will not damage native tissue of the patient during withdrawal of the delivery device from the patient.

Although prosthetic heart valve 1200 is shown as having a sealing member 1222 that is configured to move from an extended condition to a contracted condition similar to that shown in FIG. 8C, springs 1229 and pegs 1228 may also be used with prosthetic heart valves that are configured to move from an extended condition to an inverted condition, such as that shown in FIG. 8B.

FIG. 13A illustrates prosthetic heart valve 1300a and delivery device 1310a, which is substantially the same as prosthetic heart valve 300 and delivery device 10 of FIGS. 10A-10C. Delivery device 1310a includes sutures 1330a that extend through catheter assembly 1316a from prosthetic heart valve 1300a to handle 1320a. Handle 1320a may include a cutting mechanism (not shown) that is configured to cut end portions 1332a of sutures 1330a after inversion of sealing member 1322a. After end portions 1332a are cut, a user may grasp one end of each suture 1330a and pull the suture proximally to withdraw the suture from delivery device 1310a.

FIG. 13B illustrates prosthetic heart valve 1300b and delivery device 1310b, which is another variation of prosthetic heart valve 300 and delivery device 10 of FIGS. 10A-10C. Delivery device 1310b includes sutures 1330b that extend through shaft 1328 within catheter assembly 1316b from prosthetic heart valve 1300b to handle 1320b. Shaft 1328, which may extend through catheter assembly 1316b, may have a sharp distal end that is configured to cut sutures 1330a when the shaft is moved distally by a user after inversion of sealing member 1322a. Although FIG. 13B illustrates an example of a shaft 1328 having a sharp distal end, in other examples, the catheter assembly 1316b may include other types of cutting mechanisms. Portions of sutures 1330a may remain in the patient with the prosthetic heart valve 1300b instead of being removed. Such sutures 1330a may be biodegradable.

FIGS. 14A and 14B illustrate a prosthetic heart valve 1400 that is a variation of prosthetic heart valve 300 of FIGS. 3A-3C. Prosthetic heart valve 1400 has one or more filaments 1430, each filament having a coiled portion 1432 extending through a respective aperture in sealing member 1422 adjacent its free edge 1423. Each filament 1430 has a proximal end portion (not shown) at an end opposite the coiled portion 1432. The proximal end portions of filaments 1430 may extend through a catheter assembly to an operating handle, such as operating handle 20 of FIGS. 10A and 10B, where the proximal end portions may be available for grasping by a user. Coiled portions 1432 may each comprise a spring steel coil, or, for example, another filamentary element that has a shape memory.

When a user desires to invert sealing member 1422 from the extended condition of FIG. 14A to the inverted condition of FIG. 14B, the user may grasp the proximal end portions of filaments 1430 and pull the end portions in a proximal direction. At first, the pulling of filaments 1430 will cause the sealing member 1422 to invert, because the force required to unwind coiled portions 1432 is sufficiently large that the coiled portions will not unwind while the sealing member inverts. The user may continue to pull the end portions proximally, which will cause the coiled portions 1432 to unwind and withdraw from the respective apertures in sealing member 1422. Once the coiled portions 1432 have completely decoupled from sealing member 1422, the user may withdraw filaments 1430 from the delivery device.

FIGS. 15A and 15B illustrate prosthetic heart valve 1500 and delivery device 1510, which is a variation of prosthetic heart valve 300 and delivery device 10 of FIGS. 10A-10C. Delivery device 1510 has one or more sutures 1530, each suture having a distal end 1532 affixed to sealing member 1522 adjacent its free edge 1523, and a proximal end 1534. Each proximal end 1534 may include a loop with opening 1536 therein (FIG. 15B). In this embodiment, sutures 1530 remain in a patient with prosthetic heart valve 1500 instead of being removed. Such sutures 1530 may be biodegradable.

Delivery device 1510 includes spring arms 1526 each having a first end 1527 pivotally coupled to retainer 1525 and a second end 1528 remote from the first end. Second end 1528 of each spring arm 1526 has a hook feature that forms a radially-inwardly facing acute angle relative to the rest of the spring arm. When spring arms 1526 are covered by distal sheath 1524, the spring arms are retained within recesses 1529 of retainer 1525. When spring arms 1526 are uncovered by distal sheath 1524, the second ends of the spring arms are configured to automatically (i.e., without actuation by the user independent from actuation of distal sheath 1524) pivot away from the retainer according to their bias.

During deployment of prosthetic heart valve 1500, after distal sheath 1524 has uncovered the prosthetic heart valve, sealing member 1522 is initially in the extended condition with distal sheath covering spring arms 1526. In this initial condition, proximal ends 1534 of sutures 1530 are removably coupled to spring arms 1526 with second ends 1528 of the spring arms extending into openings 1536 of the sutures.

To invert sealing member 1522, a user may move distal sheath 1524 proximally to uncover prosthetic heart valve 1500, so that the heart valve self-expands in a radial direction. Since sutures 1530 extend along the outside surface of prosthetic heart valve 1500, the radial expansion of the prosthetic heart valve will push central portions of the sutures radially outward from a longitudinal axis of the valve, thereby shortening the distance between distal end 1532 and proximal end 1534 of each suture 1530. Since proximal end 1534 of each suture 1530 is coupled to delivery device 1510 by a respective spring arm 1526, each distal end 1532 will be moved closer to its corresponding proximal end, thereby moving sealing member 1522 to the inverted condition shown in FIG. 15B.

To release sutures 1530 from delivery device 1510, a user may move distal sheath 1524 further proximally to uncover spring arms 1526, and the spring arms will automatically pivot outwardly so that second ends 1528 are spaced apart from retainer 1525. Once spring arms 1526 have pivoted to the fully outward position shown in FIG. 15B, proximal end 1534 of each suture 1530 will slide off the hook feature at second end 1528 of the respective spring arm as a result of the continued tension applied to the sutures by the spring arms, thereby decoupling the sutures from the spring arms. Before delivery device 1510 is removed from the patient, the user may pivot spring arms 1526 back into recesses 1529 by moving distal sheath 1524 distally to cover the spring arms.

Figure 16A:
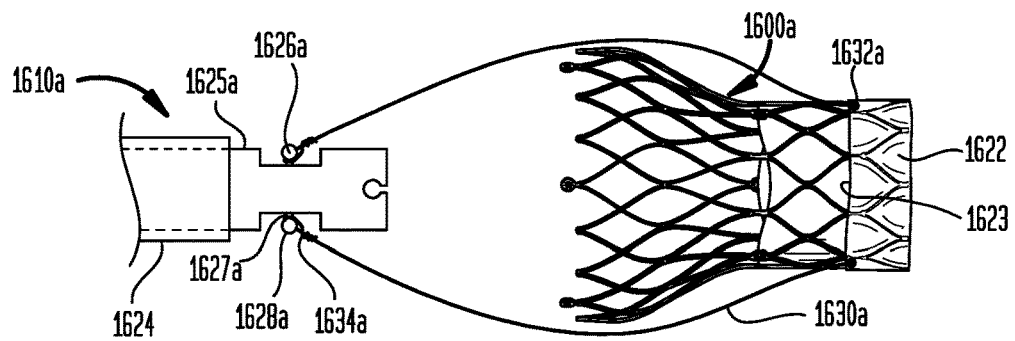
FIG. 16A is a highly schematic cross-sectional view of an embodiment of a prosthetic heart valve having a sealing member for filling irregularities between the heart valve and the native valve annulus in accordance with the present disclosure, with the sealing member in an inverted condition, shown coupled to the distal end of a delivery device.

FIG. 16A illustrates prosthetic heart valve 1600a and delivery device 1610a, which is a variation of prosthetic heart valve 1500 and delivery device 1510 of FIGS. 15A and 15B. Delivery device 1610a includes one or more sutures 1630a, each suture having a distal end 1632a affixed to sealing member 1622 adjacent its free edge 1623, and a proximal end 1634a. Each proximal end 1634a may include a loop having an opening therein.

Delivery device 1610a includes lateral posts 1626a each having a first end 1627a affixed to retainer 1625a and a second bulbous end 1628a remote from the first end. The openings at proximal ends 1634a of sutures 1630a preferably have approximately the same diameter as the bulbous ends 1628a, so that the proximal ends of the sutures won't fall off of the bulbous ends when lateral posts 1626a are covered by distal sheath 1624, but a small amount of pulling on the sutures will pull the sutures off of the lateral posts. Therefore, when lateral posts 1626a are uncovered by distal sheath 1624, proximal ends 1634a of sutures 1630a are free to slip off of the lateral posts if a radially-outward force is applied to the proximal ends of the sutures.

Although bulbous ends 1628a are shown as having a bulb shape, any shape of second ends 1628a may be used that can removably retain proximal ends 1634a of sutures 1630a on lateral posts 1626a while distal sheath 1624 is covering the lateral posts, and that can permit the proximal ends of the sutures to be easily pulled off of the lateral posts when the distal sheath uncovers the lateral posts.

During deployment of prosthetic heart valve 1600a, after distal sheath 1624 has uncovered the prosthetic heart valve, sealing member 1622 is initially in the extended condition with the distal sheath covering lateral posts 1626a. In this initial condition, proximal ends 1634a of sutures 1630a are removably coupled to lateral posts 1626a with the bulbous ends 1628a of the lateral posts extending through the openings of the proximal ends of the sutures.

To invert sealing member 1622, a user may move distal sheath 1624 proximally to uncover prosthetic heart valve 1600a, so that the heart valve self-expands in a radial direction. Since sutures 1630a extend along the outside surface of prosthetic heart valve 1600a, the radial expansion of the prosthetic heart valve will push central portions of the sutures radially outward from a longitudinal axis of the valve, thereby shortening the distance between distal end 1632a and proximal end 1634a of each suture 1630a. Since proximal end 1634a of each suture 1630a is coupled to delivery device 1610a by a respective lateral post 1626a, each distal end 1632a will be moved closer to its corresponding proximal end, thereby moving sealing member 1622 to the inverted condition shown in FIG. 16A.

To release sutures 1630a from delivery device 1610a, once sealing member 1622 has inverted, the user may continue to move distal sheath 1624 proximally to uncover lateral posts 1626a. The continued radially-outward force applied by prosthetic heart valve 1600a to central portions of sutures 1630a will push proximal ends 1634a of the sutures off of lateral posts 1626a, thereby decoupling the valve from delivery device 1610a. In this embodiment, sutures 1630a remain in a patient with prosthetic heart valve 1600a instead of being removed. Such sutures 1630a may be biodegradable.

Figure 16B:
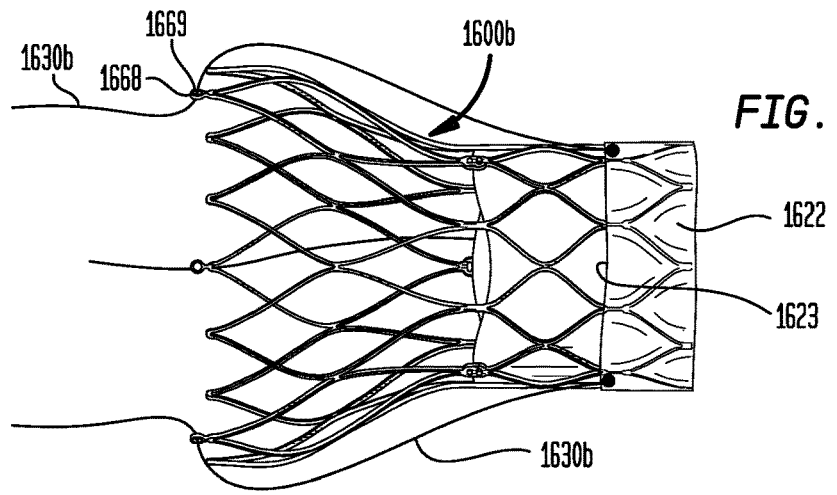
FIG. 16B is a highly schematic cross-sectional view of a variant of the prosthetic heart valve of FIG. 16A, with the sealing member in an inverted condition.

FIG. 16B illustrates a prosthetic heart valve 1600b that is a variation of prosthetic heart valve 1600a of FIG. 16A. Prosthetic heart valve 1600b is the same as prosthetic heart valve 1600a, except that prosthetic heart valve 1600b has sutures 1630b that extend through openings 1669 in stent retaining elements 1668 during the path from free edge 1623 of sealing member 1622 to the retainer of a delivery device, such as delivery device 1610a of FIG. 16A. Since sutures 1630b extend through openings 1669 in stent retaining elements 1668, when prosthetic heart valve 1600b is uncovered and radially self-expands, the sutures may more easily maintain their circumferentially-spaced positions about the valve. Such a configuration may result in a more reliable and repeatable inversion of sealing member 1622 than the embodiment of FIG. 16A. In such embodiment, when sutures 1630b are detached as described above in the previous embodiment, the sutures remain attached to prosthetic heart valve 1600b and may biodegrade over time.

Figure 16C:
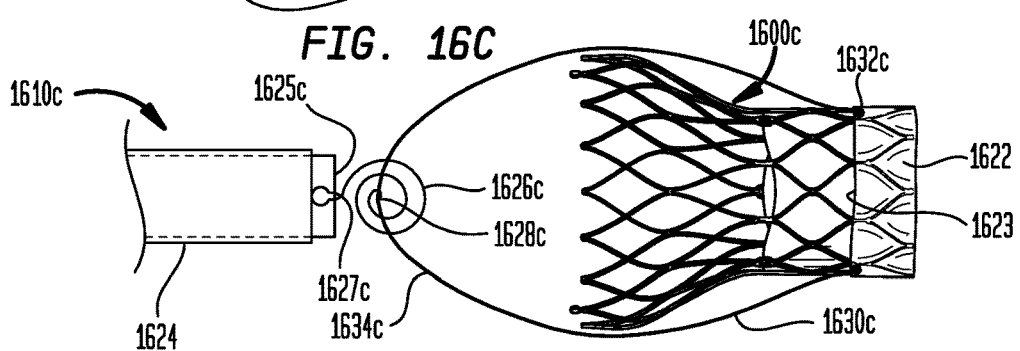
FIG. 16C is a highly schematic cross-sectional view of another variant of the prosthetic heart valve of FIG. 16A, with the sealing member in an inverted condition, shown coupled to the distal end of a delivery device.

FIG. 16C illustrates prosthetic heart valve 1600c and delivery device 1610c, which is another variation of prosthetic heart valve 1500 and delivery device 1510 of FIGS. 15A and 15B. Delivery device 1610c has one or more sutures 1630c, each suture having a distal end 1632c affixed to sealing member 1622 adjacent its free edge 1623, and a proximal end 1634c. Each proximal end 1634c may form a loop having an opening therein.

Delivery device 1610c includes one or more coiled filaments 1626c having a first end 1627c affixed to retainer 1625c and a second free end 1628c at the end of the coil. The coiled filament 1626c may comprise a spring steel coil, or, for example, another filamentary element that has a shape memory.

During deployment of prosthetic heart valve 1600c, sealing member 1622 is initially in the extended condition with distal sheath 1624 covering the valve. In this initial condition, proximal ends 1634c of sutures 1630c are removably coupled to one or more coiled filaments 1626c with free ends 1628c of the coiled filaments extending into the openings at the proximal ends of the sutures.

To invert sealing member 1622, a user may move distal sheath 1624 proximally to uncover prosthetic heart valve 1600c, so that the heart valve self-expands in a radial direction. Since sutures 1630c extend along the outside of prosthetic heart valve 1600c, the radial expansion of the prosthetic heart valve will push central portions of the sutures radially outward from the longitudinal axis of the valve, thereby shortening the distance between distal end 1632c and proximal end 1634c of each suture 1630c. Since proximal ends 1634c of sutures 1630c are coupled to delivery device 1610c by one or more coiled filaments 1626c, each distal end 1632a will be moved closer to its corresponding proximal end, thereby moving sealing member 1622 to the inverted condition shown in FIG. 16C.

Once sealing member 1622 has inverted, the user may decouple proximal ends 1634c of sutures 1630c from the one or more coiled filaments 1626c by pulling delivery device 1610c in a proximal direction. Because the frictional force between prosthetic heart valve 1600c and the native anatomy will be greater than the force required to unwind coiled filaments 1626c, as the user pulls delivery device 1610c proximally, the coiled filaments will unwind and withdraw from the openings in proximal ends 1634c of sutures 1630c, thereby decoupling the valve from the delivery device.

Figure 17:
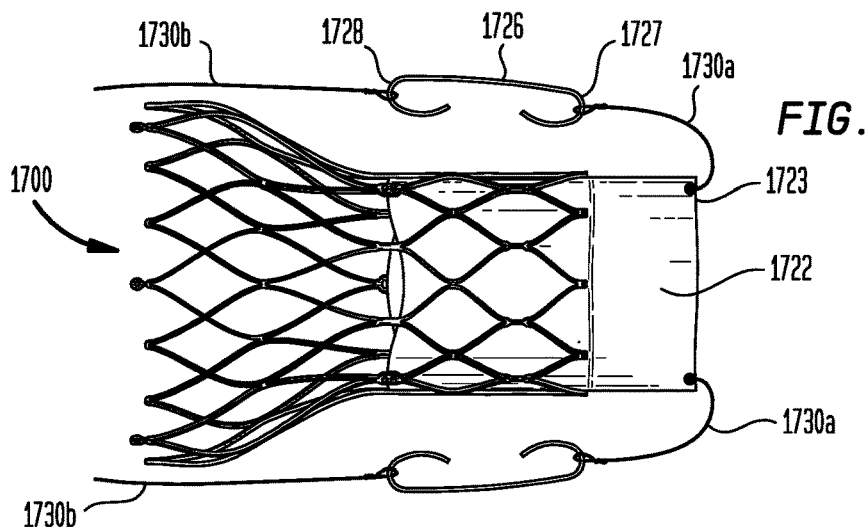
FIG. 17 is a highly schematic cross-sectional view of an embodiment of a prosthetic heart valve having a sealing member for filling irregularities between the heart valve and the native valve annulus in accordance with the present disclosure, with the sealing member in an inverted condition.

FIG. 17 illustrates prosthetic heart valve 1700, which is a variation of prosthetic heart valve 1600c of FIG. 16C. Prosthetic heart valve 1700 is the same as prosthetic heart valve 1600c, except that sutures 1730 include coiled links 1726 in a central portion thereof.

Each suture 1730 has a distal portion 1730a extending between free edge 1723 of sealing member 1722 and a first end 1727 of a corresponding coiled link 1726, and a proximal portion 1730b extending between a second end 1728 of the corresponding coiled link 1726 and the retainer of a delivery device, such as delivery device 1610c. The distal portion 1730a of suture 1730 forms a loop having an opening therein that is configured to have first end 1727 of coiled link 1726 extend therethrough. Proximal portion 1730b of suture 1730 also forms a loop having an opening therein that is configured to have second end 1728 of coiled link 1726 extend therethrough. Each coiled link 1726 may comprise a portion of a spring steel coil.

To ensure that link 1726 may disengage from distal portion 1730a of suture 1730 to release prosthetic heart valve 1700 from a delivery device, second end 1728 of the link may be fixedly connected to proximal portion 1730b of the suture, for example, using an adhesive. Alternatively, second end 1728 of link 1726 may form a closed loop or may incorporate a boss having a width greater than a diameter of the looped end of proximal portion 1730b of suture 1730, such that the proximal portion of the suture may be fixedly retained on the second end of the link.

The deployment of prosthetic heart valve 1700 is performed identically to the deployment of prosthetic heart valve 1600c described above, except that once sealing member 1722 has inverted, the user may decouple distal portions 1730a of sutures 1730 from the corresponding coiled links 1726 by pulling the delivery device in a proximal direction. Because the frictional force between the prosthetic heart valve 1700 and the native anatomy will be greater than the force required to unwind first end 1727 of coiled links 1726, as the user pulls the delivery device proximally, the first ends of the coiled links will unwind and withdraw from the openings in distal portions 1730a of sutures 1730, thereby decoupling the valve from the delivery device.

Figure 18A:
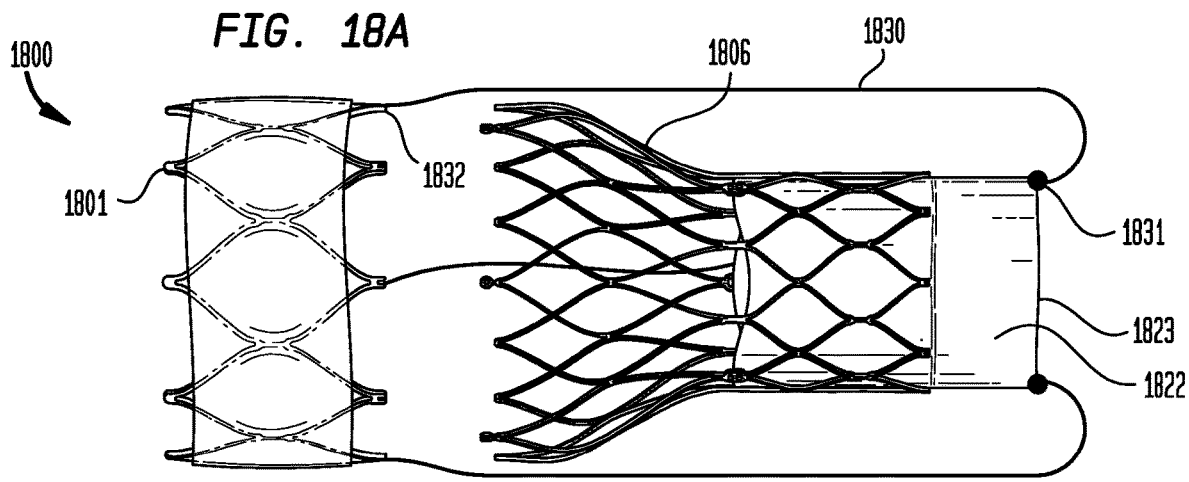
FIG. 18A is a highly schematic cross-sectional view of an embodiment of a prosthetic heart valve having a sealing member for filling irregularities between the heart valve and the native valve annulus in accordance with the present disclosure, having an expandable anchor portion, with the sealing member in an extended condition.
Figure 18B:
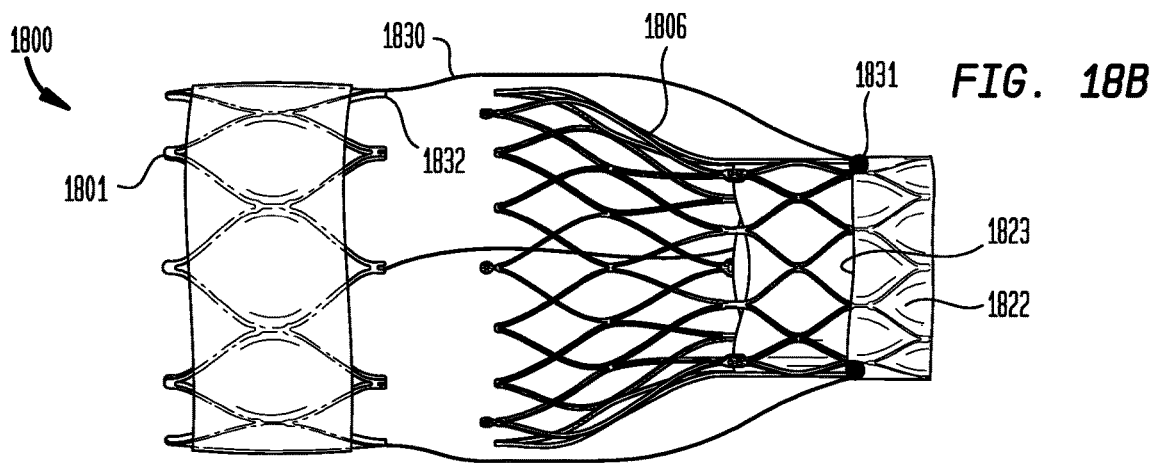
FIG. 18B is a highly schematic cross-sectional view of the prosthetic heart valve of FIG. 18A, with the sealing member in an inverted condition.
Figure 18C:
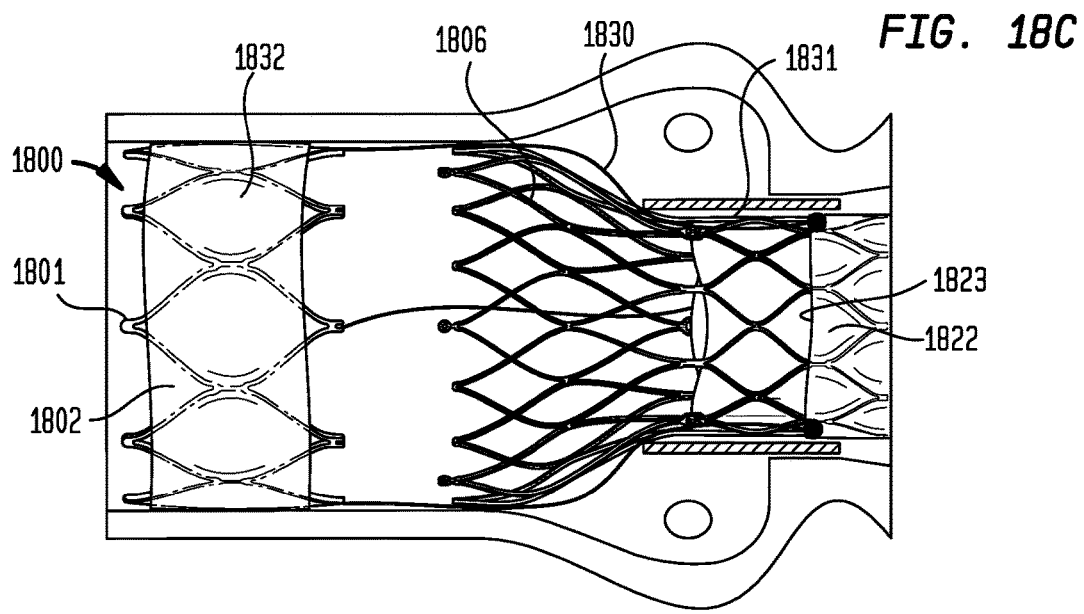
FIG. 18C is a highly schematic side view in partial cross-section showing the prosthetic heart valve of FIG. 18B in a deployed position within the native aortic annulus and ascending aorta of a patient.

FIGS. 18A-18C illustrate a prosthetic heart valve 1800 that is a variation of prosthetic heart valve 300 of FIGS. 3A-3C. Prosthetic heart valve 1800 has stent portion 1806 configured to be deployed within the native aortic annulus of a patient, and an expandable anchor portion 1801 configured to be deployed within the ascending aorta as shown in FIG. 18C. Anchor portion 1801 may have covering 1802 made of a porous fabric suitable for tissue ingrowth, for example.

Prosthetic heart valve 1800 has one or more filaments 1830 (e.g., wires, sutures, or any of the other filamentary structures described above) each having a first end 1831 affixed to sealing member 1822 adjacent its free edge 1823, and a second end 1832 affixed to anchor portion 1801. When prosthetic heart valve 1800 is in its expanded state, anchor portion 1801 retains sealing member 1822 in its inverted condition via filaments 1830 extending between the anchor portion and stent portion 1806. In one embodiment, filaments 1830 may take the form of sutures. Filaments 1830 may be biodegradable sutures that may dissolve once tissue ingrowth is sufficient to retain anchor portion 1801 and stent portion 1806 in their deployed locations.

During deployment of prosthetic heart valve 1800, sealing member 1822 is initially in the extended condition shown in FIG. 18A with the distal sheath of a delivery device (e.g., the delivery device 10 of FIGS. 10A and 10B) covering stent portion 1806 and anchor portion 1801. To deploy stent portion 1806, a user may move the distal sheath proximally to uncover prosthetic heart valve 1800, so that the heart valve self-expands in a radial direction, while anchor portion 1801 remains covered by the distal sheath.

To invert sealing member 1822, the user may pull the delivery device in a proximal direction. Because the frictional force between stent portion 1806 and the native anatomy will be greater than the force required to invert sealing member 1822, as the user pulls the delivery device proximally, sutures 1830 will move the sealing member to the inverted condition shown in FIGS. 18B and 18C.

Once sealing member 1822 has been inverted, the user may deploy anchor portion 1801 by continuing to move the distal sheath proximally to uncover the anchor portion, so that the anchor portion self-expands in a radial direction. Once anchor portion 1801 has been deployed, the delivery device may be removed from the patient.

Although various sealing structures have been described herein as "sealing rings," it is to be understood that the term "sealing ring" as used herein may describe one or more discontinuous sealing structures that do not completely extend around the circumference of the stent of a prosthetic heart valve.

Although many of the embodiments herein have been described as having sutures, any of such sutures may be replaced with other filamentary elements, such as at least one polymer wire, braided metal wire, Nitinol wire, cord, ribbon, or any other connecting member that may be used to pull the corresponding sealing member to an inverted condition or a contracted condition.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

In summary, the disclosure herein recites multiple embodiments. Described herein is a prosthetic heart valve configured to be expanded proximate a native valve of a patient. The prosthetic heart valve may include a collapsible and expandable stent having a proximal end, a distal end, an annulus section adjacent the proximal end, and a plurality of cells connected to one another in a plurality of annular rows around the stent, a cuff attached to the annulus section of the stent and defining an outward-facing surface, a plurality of prosthetic valve leaflets attached to the cuff, and a sealing member attached to the cuff and extending from a proximal end of the cuff to a free edge. The stent may have a flow direction extending from the proximal end of the stent toward the distal end of the stent. The sealing member may be movable between an extended condition in which the free edge is located proximally of the proximal end of the stent, and an inverted condition in which the free edge is located distally of the proximal end of the stent and a first surface of the sealing member confronts the outward-facing surface of the cuff; and/or the sealing member in the extended condition may be located entirely below the proximal end of the stent; and/or the sealing member in the inverted condition may extend continuously around a circumference of the stent; and/or the prosthetic heart valve may also include a sealing ring attached to a second surface of the sealing member opposite the first surface, wherein in the inverted condition of the sealing member and in an expanded use condition of the stent, the sealing ring may have a diameter greater than a diameter of the proximal end of the stent; and/or in the extended condition of the sealing member, the sealing ring may be located entirely proximally of the proximal end of the stent; and/or the prosthetic heart valve may also include a stored energy element inside the sealing ring, wherein in the inverted condition of the sealing member the stored energy element is biased to provide a force to an outer edge of the sealing ring in a direction orthogonal to the flow direction when the outer edge is radially compressed; and/or the stored energy element may include a spring that extends in at least one complete loop about a circumference of the sealing ring; and/or the prosthetic heart valve may also include a plurality of retractable wires extending between a first position on the stent and a second position near the free edge of the sealing member, the retractable wires having a first length in the extended condition of the sealing member and a second length in the inverted condition of the sealing member, the second length being shorter than the first length.

Also described herein is another prosthetic heart valve configured to be expanded proximate a native valve of a patient. The prosthetic heart valve may include a collapsible and expandable stent having a proximal end, a distal end, an annulus section adjacent the proximal end, and a plurality of cells connected to one another in a plurality of annular rows around the stent, a cuff attached to the annulus section of the stent and defining an outward-facing surface, a plurality of prosthetic valve leaflets attached to the cuff, and a sealing member attached to the cuff and extending from a proximal end of the cuff to a free edge. The stent may have a flow direction extending from the proximal end of the stent toward the distal end of the stent. The sealing member may be movable between an extended condition in which the free edge is located a first distance proximally of the proximal end of the stent, and a compressed condition in which the free edge is located a second distance proximally of the proximal end of the stent; and/or in the compressed condition of the sealing member and in an expanded use condition of the stent, the sealing member may have a diameter greater than a diameter of the proximal end of the stent; and/or in the compressed condition of the sealing member and in an expanded use condition of the stent, the sealing member may have a plurality of alternating peaks and valleys extending in the circumferential direction of the stent, the peaks being located at a greater radial distance away from the stent than the valleys; and/or in the compressed condition of the sealing member and in the expanded use condition of the stent, each of the peaks may have an adjacent valley proximal to at least a portion of the respective peak, and each of the peaks may have a central portion that extends proximally of the respective adjacent valley.

Also described herein is a method of expanding a prosthetic heart valve proximate a native valve of a patient. The prosthetic heart valve may include a stent having proximal and distal ends, a cuff attached to the stent, and a sealing member extending from a proximal end of the cuff to a free edge.

The method may include collapsing the prosthetic heart valve into a delivery device such that the sealing member is in an extended condition in which the free edge is located proximally of the proximal end of the stent, inserting the delivery device into a patient, advancing the delivery device proximate an annulus of the native valve, partially expanding the prosthetic heart valve in a selected position proximate the native valve, moving the sealing member from the extended condition to an inverted condition in which the free edge is located distally of the proximal end of the stent, and fully expanding the prosthetic heart valve; and/or the sealing member in the extended condition may be located entirely proximally of the proximal end of the stent; and/or the sealing member may include wires extending from the free end of the sealing member through the delivery device to a location outside the patient, and the moving step may include pulling the wires to move the free edge of the sealing member; and/or the method may also include withdrawing the wires from the patient while leaving the prosthetic heart valve inside the patient; and/or after the moving step, a first surface of the sealing member may confront an outward-facing surface of the cuff; and/or the prosthetic heart valve may also include a sealing ring attached to a second surface of the sealing member opposite the first surface, and the moving step may include inverting the sealing ring from an inward-facing condition to an outward-facing condition in which the sealing ring has a diameter greater than a diameter of the proximal end of the stent; and/or in the extended condition of the sealing member, the sealing ring may be located entirely proximally of the proximal end of the stent; and/or the sealing member may include wires extending between a first position on the stent and a second position near the free edge of the sealing member, the collapsing step may include extending the wires to a first length, and the moving step may include contracting the wires to a second length shorter than the first length.

Also described herein is a system including a delivery device and a prosthetic heart valve. The delivery device may include an operating handle and a catheter assembly. The catheter assembly may include a first shaft around which a compartment is defined, the first shaft being operatively connected to the operating handle, and a distal sheath at least partially surrounding the first shaft, the distal sheath being moveable between a closed condition covering the compartment and an open condition uncovering the compartment for deployment of the valve.

The prosthetic heart valve may be mounted in the compartment. The prosthetic valve may include a collapsible and expandable stent, a cuff, and a sealing member attached to the cuff. The stent may have a proximal end, a distal end, and an annulus section adjacent the proximal end, the stent having a flow direction extending from the proximal end toward the distal end. The cuff may be attached to the annulus section of the stent and may define an outward-facing surface.

The sealing member may extend from a proximal end of the cuff to a free edge, the sealing member being movable between an extended condition in which the free edge is located at a first location proximally of the proximal end of the stent, and a use condition in which the free edge is located at a second location distally of the first location and a first surface of the sealing member confronts the outward-facing surface of the cuff. The sealing member may have an energy storage element with a bias to move the sealing member toward the use condition. The catheter assembly may have a restraining member removably coupled to the sealing member to hold the sealing member in the extended condition against the bias of the energy storage element; and/or the restraining member may be a peg affixed to a wire, the wire extending through the catheter assembly to the operating handle; and/or the restraining member may be a peg affixed to a second energy storage element that extends between the peg and the distal sheath, and the second energy storage element may be configured to store energy when the distal sheath is moved toward the operating handle; and/or the restraining member may be coupled to the valve by filaments that are configured to break when the distal sheath is moved toward the operating handle beyond a predetermined distance.

Also described herein is another system including a delivery device and a prosthetic heart valve. The delivery device may include an operating handle and a catheter assembly. The catheter assembly may include a first shaft around which a compartment is defined, the first shaft being operatively connected to the operating handle, and a distal sheath at least partially surrounding the first shaft, the distal sheath being moveable between a closed condition covering the compartment and an open condition uncovering the compartment for deployment of the valve.

The prosthetic heart valve may be mounted in the compartment. The prosthetic valve may include a collapsible and expandable stent, a cuff, and a sealing member attached to the cuff. The stent may have a proximal end, a distal end, and an annulus section adjacent the proximal end, the stent having a flow direction extending from the proximal end toward the distal end. The cuff may be attached to the annulus section of the stent and may define an outward-facing surface.

The sealing member may extend from a proximal end of the cuff to a free edge, the sealing member being movable between an extended condition in which the free edge is located at a first location proximally of the proximal end of the stent, and a use condition in which the free edge is located at a second location distally of the first location and a first surface of the sealing member confronts the outward-facing surface of the cuff. The catheter assembly may have an actuating filament having a portion removably coupled to the sealing member and configured to move the sealing member from the extended condition to the use condition when the portion of the actuating filament is moved toward the operating handle; and/or the actuating filament may be configured to move the sealing member from the extended condition to the use condition when the entire actuating filament is pulled toward the operating handle; and/or the actuating filament may be configured to move the sealing member from the extended condition to the use condition when the portion of the actuating filament is moved toward the operating handle by a first distance, and may be configured to decouple from the sealing member when the portion of the actuating filament is moved toward the operating handle by a second distance greater than the first distance; and/or the actuating filament may include a coiled spring portion that is configured to unwind when the portion of the actuating filament is moved toward the operating handle by the second distance; and/or the actuating filament may include a proximal portion operatively coupled to the distal sheath, and a distal portion operatively coupled to the sealing member, and the coiled spring portion may removably couple the proximal portion to the distal portion.

Also described herein is another system including a delivery device and a prosthetic heart valve. The delivery device may include an operating handle and a catheter assembly. The catheter assembly may include a first shaft around which a compartment is defined, the first shaft being operatively connected to the operating handle, and a distal sheath at least partially surrounding the first shaft, the distal sheath being moveable between a closed condition covering the compartment and an open condition uncovering the compartment for deployment of the valve.

The prosthetic heart valve may be mounted in the compartment. The prosthetic valve may include a collapsible and expandable stent, a cuff, and a sealing member attached to the cuff. The stent may have a proximal end, a distal end, and an annulus section adjacent the proximal end, the stent having a flow direction extending from the proximal end toward the distal end. The cuff may be attached to the annulus section of the stent and may define an outward-facing surface.

The sealing member may extend from a proximal end of the cuff to a free edge, the sealing member being movable between an extended condition in which the free edge is located at a first location proximally of the proximal end of the stent, and a use condition in which the free edge is located at a second location distally of the first location and a first surface of the sealing member confronts the outward-facing surface of the cuff. The catheter assembly may have an actuating filament removably coupled to a retaining element of the catheter assembly and configured to move the sealing member from the extended condition to the use condition when a portion of the actuating filament is moved toward the operating handle; and/or a proximal end of the actuating filament may be removably coupled to the delivery device, and the actuating filament may be configured to move the sealing member from the extended condition to the use condition when the portion of the actuating filament is moved toward the proximal end of the actuating filament; and/or the delivery device may also include a cutting tool configured to decouple at least a portion of the actuating filament from the retaining element, the portion of the actuating filament being biodegradable; and/or the retaining element may be a pivotable arm configured to retain a proximal end of the actuating filament when the arm is covered by the distal sheath, and to release the proximal end of the actuating filament when the distal sheath is moved proximally to uncover the arm; and/or the retaining element may be a post extending away from the first shaft in a lateral direction of the catheter assembly, the post being configured to retain a proximal end of the actuating filament when the post is covered by the distal sheath and configured to release the proximal end of the actuating filament when the distal sheath is moved proximally to uncover the post.

Also described herein is another system including a delivery device and a prosthetic heart valve. The delivery device may include an operating handle and a catheter assembly. The catheter assembly may include a first shaft around which a compartment is defined, the first shaft being operatively connected to the operating handle, and a distal sheath at least partially surrounding the first shaft, the distal sheath being moveable between a closed condition covering the compartment and an open condition uncovering the compartment for deployment of the valve.

The prosthetic heart valve may be mounted in the compartment. The prosthetic valve may include a collapsible and expandable stent, a cuff, a sealing member attached to the cuff, an expandable anchor portion having a generally cylindrical shape, and an actuating filament. The stent may have a proximal end, a distal end, and an annulus section adjacent the proximal end, the stent having a flow direction extending from the proximal end toward the distal end. The cuff may be attached to the annulus section of the stent and may define an outward-facing surface.

The sealing member may extend from a proximal end of the cuff to a free edge, the sealing member being movable between an extended condition in which the free edge is located at a first location proximally of the proximal end of the stent, and a use condition in which the free edge is located at a second location distally of the first location and a first surface of the sealing member confronts the outward-facing surface of the cuff. The actuating filament may extend between the free edge of the sealing member and the expandable anchor portion, the actuating filament configured to move the sealing member from the extended condition to the use condition when the expandable anchor portion is moved toward the operating handle; and/or the anchor portion may comprise a covering including a porous material configured to receive tissue ingrowth; and/or the sealing member may include a porous material configured to receive tissue ingrowth, and the actuating filament may be biodegradable.

Also described herein is a method of expanding a prosthetic heart valve proximate a native valve of a patient. The prosthetic heart valve may include a stent having proximal and distal ends, a cuff attached to the stent, and a sealing member extending from a proximal end of the cuff to a free edge.

The method may include collapsing the prosthetic heart valve into a delivery device such that the sealing member is in an extended condition in which the free edge is located proximally of the proximal end of the stent, inserting the delivery device into a patient, advancing the delivery device proximate an annulus of the native valve, expanding the prosthetic heart valve from a first diameter to a second diameter greater than the first diameter in a selected position proximate the native valve, and moving the sealing member from the extended condition to a use condition in which the free edge is located at a second location distally of the first location; and/or the steps of expanding the prosthetic heart valve and moving the sealing member may be performed simultaneously; and/or the step of moving the sealing member may be performed by removing a restraining member from the sealing member to permit an energy storage element of the sealing member to move the sealing member to the use condition; and/or the step of moving the sealing member may be performed by moving a portion of an actuating filament toward an operating handle of the delivery device by a first distance; and/or the method may also include decoupling the actuating filament from the prosthetic heart valve by moving the portion of the actuating filament toward the operating handle by a second distance greater than the first distance.

The invention claimed is:

1. A system comprising:
   a delivery device comprising:
      an operating handle; and
      a catheter assembly, including:
         a first shaft around which a compartment is defined, the first shaft being operatively connected to the operating handle; and
         a distal sheath at least partially surrounding the first shaft, the distal sheath being moveable between a closed condition covering the compartment and an open condition uncovering the compartment for deployment of a prosthetic heart valve; and
   a prosthetic heart valve mounted in the compartment, the prosthetic valve comprising:
      a collapsible and expandable stent having a proximal end, a distal end, and an annulus section adjacent the proximal end, the stent having a flow direction extending from the proximal end toward the distal end;
      a cuff attached to the annulus section of the stent and defining an outward-facing surface; and
      a sealing member attached to the cuff and extending from a proximal end of the cuff to a free edge, the sealing member being movable between an extended condition in which the free edge is located at a first location proximally of the proximal end of the stent, and a use condition in which the free edge is located at a second location distally of the first location and a first surface of the sealing member confronts the outward-facing surface of the cuff, the sealing member having an energy storage element with a bias to move the sealing member toward the use condition,
   wherein the catheter assembly has a restraining member removably coupled to the sealing member to hold the sealing member in the extended condition against the bias of the energy storage element.

2. The system of claim 1, wherein the restraining member is a peg affixed to a wire, the wire extending through the catheter assembly to the operating handle.

3. The system of claim 1, wherein the restraining member is a peg affixed to a second energy storage element that extends between the peg and the distal sheath, and the second energy storage element is configured to store energy when the distal sheath is moved toward the operating handle.

4. The system of claim 1, wherein the restraining member is coupled to the valve by filaments that are configured to break when the distal sheath is moved toward the operating handle beyond a predetermined distance.

5. A system comprising:
   a delivery device comprising:
      an operating handle; and
      a catheter assembly, including:
         a first shaft around which a compartment is defined, the first shaft being operatively connected to the operating handle; and
         a distal sheath at least partially surrounding the first shaft, the distal sheath being moveable between a closed condition covering the compartment and an open condition uncovering the compartment for deployment of a prosthetic heart valve; and
   a prosthetic heart valve mounted in the compartment, the prosthetic heart valve comprising:
      a collapsible and expandable stent having a proximal end, a distal end, and an annulus section adjacent the proximal end, the stent having a flow direction extending from the proximal end toward the distal end;
      a cuff attached to the annulus section of the stent and defining an outward-facing surface; and
      a sealing member attached to the cuff and extending from a proximal end of the cuff to a free edge, the sealing member being movable between an extended condition in which the free edge is located at a first location proximally of the proximal end of the stent, and a use condition in which the free edge is located at a second location distally of the first location and a first surface of the sealing member confronts the outward-facing surface of the cuff,
   wherein the catheter assembly has an actuating filament having a portion removably coupled to the sealing member and configured to move the sealing member from the extended condition to the use condition when the portion of the actuating filament is moved toward the operating handle.

6. The system of claim 5, wherein the actuating filament is configured to move the sealing member from the extended condition to the use condition when the entire actuating filament is pulled toward the operating handle.

7. The system of claim 5, wherein the actuating filament is configured to move the sealing member from the extended condition to the use condition when the portion of the actuating filament is moved toward the operating handle by a first distance, and is configured to decouple from the sealing member when the portion of the actuating filament is moved toward the operating handle by a second distance greater than the first distance.

8. The system of claim 7, wherein the actuating filament includes a coiled spring portion that is configured to unwind when the portion of the actuating filament is moved toward the operating handle by the second distance.

9. The system of claim 8, wherein the actuating filament includes a proximal portion operatively coupled to the distal sheath, and a distal portion operatively coupled to the sealing member, and the coiled spring portion removably couples the proximal portion to the distal portion.

10. A system comprising:
a delivery device comprising:
an operating handle; and
a catheter assembly, including:
a first shaft around which a compartment is defined, the first shaft being operatively connected to the operating handle; and
a distal sheath at least partially surrounding the first shaft, the distal sheath being moveable between a closed condition covering the compartment and an open condition uncovering the compartment for deployment of a prosthetic heart valve; and
a prosthetic heart valve mounted in the compartment, the prosthetic valve comprising:
a collapsible and expandable stent having a proximal end, a distal end, and an annulus section adjacent the proximal end, the stent having a flow direction extending from the proximal end toward the distal end;
a cuff attached to the annulus section of the stent and defining an outward-facing surface; and
a sealing member attached to the cuff and extending from a proximal end of the cuff to a free edge, the sealing member being movable between an extended condition in which the free edge is located at a first location proximally of the proximal end of the stent, and a use condition in which the free edge is located at a second location distally of the first location and a first surface of the sealing member confronts the outward-facing surface of the cuff,
wherein the prosthetic valve has an actuating filament removably coupled to a retaining element of the catheter assembly and configured to move the sealing member from the extended condition to the use condition when a portion of the actuating filament is moved toward the operating handle.

11. The system of claim 10, wherein a proximal end of the actuating filament is removably coupled to the delivery device, and the actuating filament is configured to move the sealing member from the extended condition to the use condition when the portion of the actuating filament is moved toward the proximal end of the actuating filament.

12. The system of claim 10, wherein the delivery device further comprises a cutting tool configured to decouple at least a portion of the actuating filament from the retaining element, the portion of the actuating filament being biodegradable.

13. The system of claim 10, wherein the retaining element is a pivotable arm configured to retain a proximal end of the actuating filament when the arm is covered by the distal sheath, and to release the proximal end of the actuating filament when the distal sheath is moved proximally to uncover the arm.

14. The system of claim 10, wherein the retaining element is a post extending away from the first shaft in a lateral direction of the catheter assembly, the post being configured to retain a proximal end of the actuating filament when the post is covered by the distal sheath and configured to release the proximal end of the actuating filament when the distal sheath is moved proximally to uncover the post.

* * * * *